United States Patent
Glushakov et al.

(10) Patent No.: US 11,789,970 B2
(45) Date of Patent: *Oct. 17, 2023

(54) GRAPH-BASED DISCOVERY OF GEOMETRY OF CLINICAL DATA TO REVEAL COMMUNITIES OF CLINICAL TRIAL SUBJECTS

(71) Applicant: Intego Group, LLC, Maitland, FL (US)

(72) Inventors: Sergey Glushakov, Orlando, FL (US); Kostiantyn Drach, Marseilles (FR); Viktoriia Shevtsova, Kharkov (UA); Iryna Kotenko, Kharkov (UA); Lyudmyla Polyakova, Kharkov (UA)

(73) Assignee: INTEGO GROUP, LLC, Maitland, FL (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/380,472

(22) Filed: Jul. 20, 2021

(65) Prior Publication Data
US 2021/0349914 A1    Nov. 11, 2021

Related U.S. Application Data

(63) Continuation-in-part of application No. 16/147,640, filed on Sep. 29, 2018, now Pat. No. 11,069,447.

(51) Int. Cl.
*G06F 16/26* (2019.01)
*G16H 10/20* (2018.01)
(Continued)

(52) U.S. Cl.
CPC ............ *G06F 16/26* (2019.01); *G06V 10/762* (2022.01); *G06V 10/7715* (2022.01);
(Continued)

(58) Field of Classification Search
CPC ... G16H 50/70; G06F 16/904; G06F 16/9024; G06F 16/9038; G06F 2216/03; G06N 20/00; G06K 9/6248
(Continued)

(56) References Cited

U.S. PATENT DOCUMENTS

| 2011/0173189 A1* | 7/2011 | Singh | G06F 16/9024 |
| | | | 707/722 |
| 2015/0127650 A1* | 5/2015 | Carlsson | G06F 16/3334 |
| | | | 707/737 |

(Continued)

*Primary Examiner* — Hicham Skhoun
(74) *Attorney, Agent, or Firm* — Georgiy L. Khayet

(57) ABSTRACT

Methods and systems for graph-based discovery of geometry of clinical data are provided. An example method includes receiving vectors of outcomes of trial subjects, generating, based on the vectors of outcomes, a plurality of metric graphs, each of the metric graphs including a set of nodes corresponding to the vectors of outcomes and a set of edges, performing an automatic search to identify communities of nodes in the optimal graph, displaying a graphical representation of the optimal graph and highlighting nodes in the graphical representation, the nodes corresponding to the community of nodes. Generating the set of edges includes selecting metrics and projection rules to obtain projections of the vectors of outcomes, and selectively connecting nodes based on determination that projections of corresponding vectors of outcomes belong to the same domain of a set of overlapping domains and a certain cluster within the domain.

20 Claims, 14 Drawing Sheets

(51) Int. Cl.
*G16H 50/70* (2018.01)
*G06V 10/762* (2022.01)
*G06V 10/77* (2022.01)
*G06V 10/84* (2022.01)

(52) U.S. Cl.
CPC ............ *G06V 10/84* (2022.01); *G16H 10/20* (2018.01); *G16H 50/70* (2018.01)

(58) Field of Classification Search
USPC ........................................................ 707/776
See application file for complete search history.

(56) References Cited

U.S. PATENT DOCUMENTS

| | | | | |
|---|---|---|---|---|
| 2016/0034561 | A1* | 2/2016 | Sexton | G06F 16/9024 707/737 |
| 2018/0285685 | A1* | 10/2018 | Singh | G06F 16/9038 |
| 2019/0361851 | A1* | 11/2019 | Rogynskyy | G06F 16/27 |
| 2019/0362809 | A1* | 11/2019 | Okimoto | G16H 50/20 |
| 2020/0167694 | A1* | 5/2020 | Pisner | G06N 5/022 |

* cited by examiner

700

```
┌─────────────────────────────────────────────────────────────────┐
│ Process, by a pre-processing module, clinical datasets to generate a first table, │
│ the first table comprising first rows representing trial subjects and first columns │
│ including outcomes of the trial subjects, and a second table, the second table │
│ comprising second rows representing the trial subjects and second columns │
│ including predictors of the trial subjects │
│ 705 │
└─────────────────────────────────────────────────────────────────┘
                                    ↓
┌─────────────────────────────────────────────────────────────────┐
│ Generate, by a graph construction module and based on the first table, one or │
│ more metric graphs, the one or more metric graphs including nodes and edges, │
│ wherein the nodes represent the trial subjects and the edges selectively │
│ connect the nodes according to one or more pre-determined criteria │
│ 710 │
└─────────────────────────────────────────────────────────────────┘
                                    ↓
┌─────────────────────────────────────────────────────────────────┐
│ Select, by the graph construction module, a graph of interest from the one or │
│ more metric graphs │
│ 715 │
└─────────────────────────────────────────────────────────────────┘
                                    ↓
┌─────────────────────────────────────────────────────────────────┐
│ Generate, by the graph construction module, a compressed version of the │
│ graph of interest, the compressed version including a clustered graph │
│ 720 │
└─────────────────────────────────────────────────────────────────┘
                                    ↓
┌─────────────────────────────────────────────────────────────────┐
│ Generate, by the graph construction module, a first layout of the graph of │
│ interest and a second layout of the compressed version of the graph of interest, │
│ the first layout and the second layout being visually aligned │
│ 725 │
└─────────────────────────────────────────────────────────────────┘
```

```
┌─────────────────────────────────────────────────────────────────────┐
│ Display, by an interactive visualization module and based on the first layout or │
│ the second layout, a graphical representation of the graph of interest │
│                                  730                                │
└─────────────────────────────────────────────────────────────────────┘
                                   ↓
┌─────────────────────────────────────────────────────────────────────┐
│ Assign, by the interactive module, colors to the nodes of the graph of interest, │
│ wherein the colors are based on a selected outcome or a selected predictor │
│                                  735                                │
└─────────────────────────────────────────────────────────────────────┘
                                   ↓
┌─────────────────────────────────────────────────────────────────────┐
│ Perform, by the interactive module and using one or more machine learning │
│ algorithms, an automatic search to identify at least one group of related trial │
│                               subjects                              │
│                                  740                                │
└─────────────────────────────────────────────────────────────────────┘
                                   ↓
┌─────────────────────────────────────────────────────────────────────┐
│ Highlight, by the interactive module, nodes in the graphical representation, the │
│ nodes corresponding to the related trial subjects                   │
│                                  745                                │
└─────────────────────────────────────────────────────────────────────┘
                                   ↓
┌─────────────────────────────────────────────────────────────────────┐
│ Receive, by the interactive visualization module and via the graphical │
│ representation, a user input, the user input including one or more selected │
│                     groups of the trial subjects                    │
│                                  750                                │
└─────────────────────────────────────────────────────────────────────┘
                                   ↓
┌─────────────────────────────────────────────────────────────────────┐
│ Perform, by the interactive visualization module configured to use the second │
│ table, a statistical analysis of predictors associated with trial subjects within the │
│         one or more selected groups of the trial subjects           │
│                                  755                                │
└─────────────────────────────────────────────────────────────────────┘
                                   ↓
┌─────────────────────────────────────────────────────────────────────┐
│ Display, by the interactive visualization module, results of the statistical │
│                               analysis                              │
│                                  760                                │
└─────────────────────────────────────────────────────────────────────┘
```

*FIG. 7*
*(Continued)*

GRAPH-BASED DISCOVERY OF GEOMETRY OF CLINICAL DATA TO REVEAL COMMUNITIES OF CLINICAL TRIAL SUBJECTS

CROSS-REFERENCE TO RELATED APPLICATION

This application is a Continuation-in-part of U.S. patent application Ser. No. 16/147,640, entitled "Systems and Methods for Topology-Based Clinical Data Mining," filed on Sep. 29, 2018. The aforementioned application is incorporated herein by reference in its entirety for all purposes.

TECHNICAL FIELD

This disclosure generally relates to clinical data processing. More specifically, this disclosure relates to systems and methods for graph-based discovery of geometry of clinical data to reveal communities of clinical trial subjects.

BACKGROUND

Clinical trials are designed and conducted to study the safety and efficacy of biomedical or behavioral interventions. Typically, only a relatively small fraction of the data collected during clinical trials is used by investigators to demonstrate the safety and efficacy of a medical intervention. However, clinical trials generate significant amounts of data that can be subsequently explored to identify unexpected factors that influence the outcomes of interest and lead to new hypotheses.

Performing a comprehensive analysis of a clinical trial dataset can be challenging. While most approaches to mining clinical data focus on univariate relationships between a specific outcome and a few predictive variables, there is a lack of data integration and visualization tools that can improve understanding of the entire dataset. Examining clinical data with a focus on a specific single outcome in isolation from other factors may lead to an incomplete, or even misleading, view of complex settings. Standard biostatistical methods can be used as technical tools to confirm (or refute) the hypotheses generated by an investigator and, therefore, depend on the researcher's ability to develop solid hypotheses. However, in the case of clinical trial datasets, the number of possible hypotheses to explore is very large, and it can be very difficult to select the most relevant.

SUMMARY

This section introduces a selection of concepts in a simplified form that are further described in the Detailed Description section, below. This summary does not identify key or essential features of the claimed subject matter and is not intended to be an aid in determining the scope of the claimed subject matter.

The methods and systems presented in this disclosure are directed to graph-based discovery of geometry of clinical data. Embodiments of the present disclosure may also provide an integrated approach that combines clinical biostatistics, topological data analysis, machine learning, and data visualization. The present technology may allow mining for hidden patterns in clinical datasets. Some embodiments of the present disclosure provide an interactive visualization application allowing researchers to explore groups of trial subjects with similar outcomes and perform statistical analysis of predictors of a trial subject within the groups.

According to one embodiment of this disclosure, the method for graph-based discovery of geometry of clinical data is provided. The method can include receiving vectors of outcomes of trial subjects. The method may include generating, based on the vectors of outcomes, a plurality of metric graphs. Each metric graph may include the same set of nodes corresponding to the vectors of outcomes and a set of edges. Generating the set of edges may include transforming the vectors of outcomes to generate data points. Generating the set of edges may include selecting a projection rule from a set of projection rules and applying the selected projection rule to the data points to obtain projections of the vectors of outcomes. Generating the set of edges may include, for each of a first node and a second node from the same set of nodes, determining that a first projection and a second projection of the projections of the data points satisfy similarity criteria, where the first projection corresponds to the first node and the second projection corresponds to the second node. Generating the set of edges may include selectively connecting, based on the determination that a first projection and a second projection satisfy the similarity criteria, the first node and the second node.

The method may include selecting, from the plurality of metric graphs, an optimal graph. The method can include performing an automatic search to identify at least one community of nodes in the optimal graph. The method can include displaying a graphical representation of the optimal graph and highlighting those nodes in the graphical representation that correspond to the community of nodes.

The transformation of the vectors of outcomes may include selecting a first metric from a set of metrics and applying the first metric to the vectors of outcomes to generate data points. The projection rule may depend on a second metric of the set of metrics, where the second metric can be different from the first metric. The set of metrics may include one or more of the following or a weighted combination of: a Euclidean distance, a normalized Euclidean distance, a Manhattan distance, a Hamming distance, a Gower distance, and a Minkowski distance. The set of metrics may include a complex metric obtained as a weighted sum of metrics determined on subsets of components of the vectors of outcomes.

The determination that the first projection and the second projection satisfy the similarity criteria may include determining that the first projection and the second projection are located within a same domain in a set of overlapping domains. Each set of the overlapping domains may have the same size. Alternatively, each set of the overlapping domains may contain the same number of the projections.

The determination that the first projection and the second projection satisfy the similarity criteria may additionally include constructing a tree of clusters of the projections belonging to the same domain and by varying a level of granularity and determining that the first projection and the second projection belong to the same cluster from the tree of clusters. The cluster can be of an optimal level of granularity obtained for the domain containing the first projection and the second projection. The optimal level of granularity may satisfy the following conditions: 1) the number of clusters corresponding to the optimal level of granularity is less than half of the total number of the projections in the domain; and 2) the number of clusters corresponding to the optimal value of granularity exceeds the minimum of a standard deviation of numbers of clusters obtained using a set of values for the level of granularity.

According to another embodiment, a system for graph-based discovery of geometry of clinical data is provided.

The system may include at least one processor and a memory storing processor-executable codes, wherein the processor can be configured to implement the operations of the above-mentioned method for graph-based discovery of geometry of clinical data.

According to yet another aspect of the disclosure, there is provided a non-transitory processor-readable medium, which stores processor-readable instructions. When the processor-readable instructions are executed by a processor, they cause the processor to implement the above-mentioned method for graph-based discovery of geometry of clinical data.

Additional objects, advantages, and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which:

FIG. 7 is a flow chart showing a method for topology-based clinical data mining, according to an example embodiment.

DETAILED DESCRIPTION OF EXAMPLE EMBODIMENTS

Figure 1:
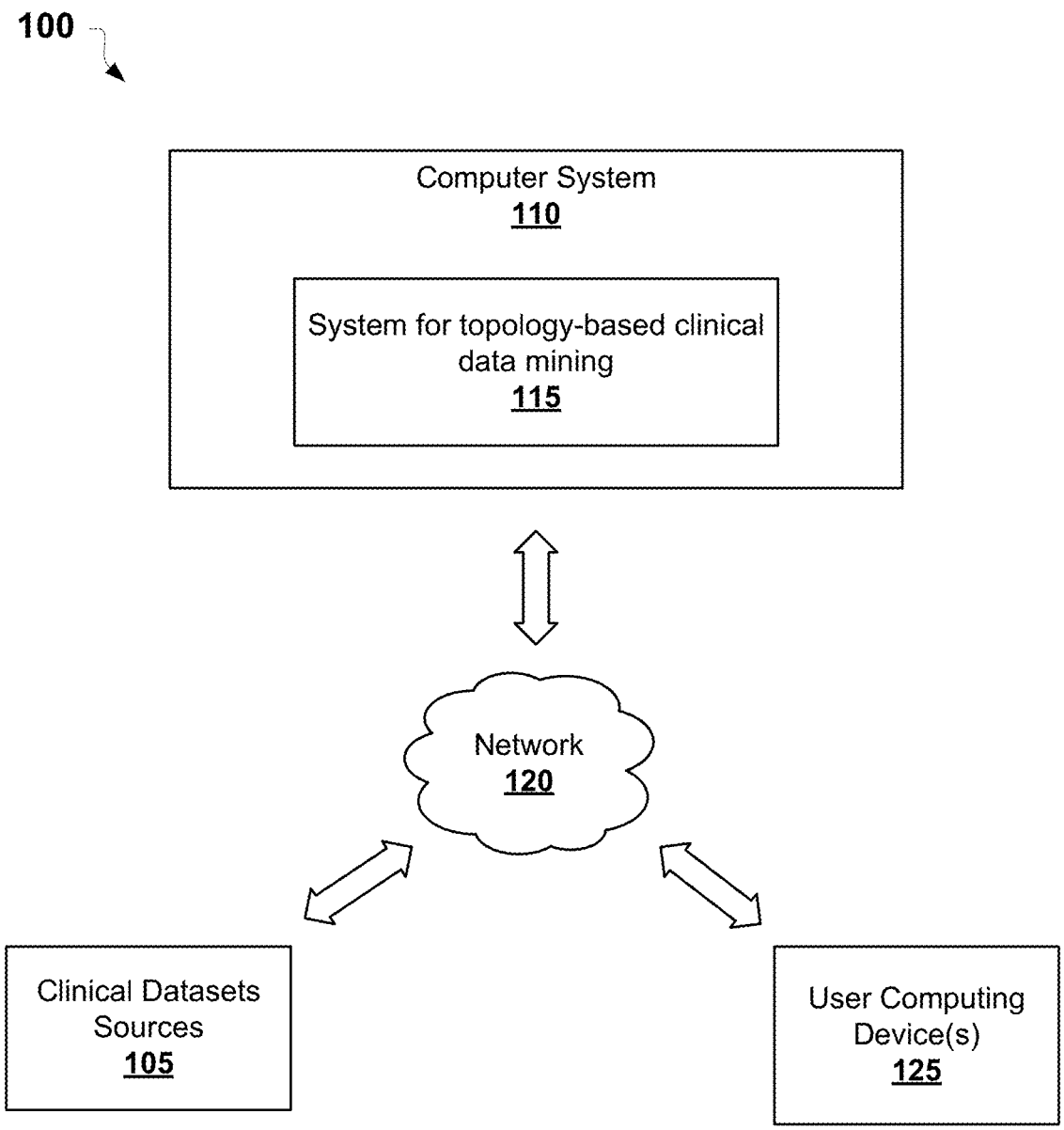
FIG. 1 is a block diagram showing an example architecture, wherein methods for topology-based clinical data mining can be implemented.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Embodiments of this disclosure are concerned with methods and systems for graph-based discovery of geometry of clinical data. The methods described herein can be implemented by hardware modules, software modules, or a combination of both. The methods can also be embodied in computer-readable instructions stored on computer-readable media. As should be evident from the following description, the methods and systems of this disclosure allow mining for hidden patterns in clinical datasets. Embodiments of the present disclosure may also provide an interactive visualization application allowing researchers to explore groups of trial subjects with similar outcomes and perform statistical analysis of predictors of trial subjects within the groups.

The embodiments will now be presented with reference to the accompanying drawings. These embodiments are described and illustrated by various modules, blocks, components, circuits, steps, operations, processes, algorithms, and the like, collectively referred to as "components" for simplicity. These components may be implemented using electronic hardware, computer software, or any combination thereof. Whether such components are implemented as hardware or software depends upon the particular application and design constraints imposed on the overall system. By way of example, a component, or any portion of a component, or any combination of components may be implemented with a "processing system" that includes one or more processors. Examples of processors include microprocessors, microcontrollers, Central Processing Units (CPUs), digital signal processors (DSPs), field programmable gate arrays (FPGAs), programmable logic devices (PLDs), state machines, gated logic, discrete hardware circuits, and other suitable hardware configured to perform various functions described throughout this disclosure. One or more processors in the processing system may execute software, firmware, or middleware (collectively referred to as "software"). The term "software" shall be construed broadly to mean instructions, instruction sets, code, code segments, program code, programs, subprograms, software components, applications, software applications, software packages, routines, subroutines, objects, executables, threads of execution, procedures, functions, and the like, whether referred to as software, firmware, middleware, microcode, hardware description language, or otherwise. The software may be stored on or encoded as one or more instructions or code on a non-transitory computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), compact disk ROM (CD-ROM) or other optical disk storage, magnetic disk storage, solid state memory, or any other data storage devices, combinations of the aforementioned types of computer-readable media, or any other medium that can be used to store computer executable code in the form of instructions or data structures that can be accessed by a computer.

For purposes of this document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

The term "module" shall be construed to mean a hardware device, software, or a combination of both. For example, a hardware-based module can use either one or more microprocessors, application-specific integrated circuits (ASICs), programmable logic devices, transistor-based circuits, or various combinations thereof. Software-based modules can constitute computer programs, computer program procedures, computer program functions, and the like. In addition, a module of a system can be implemented by a computer or server, or by multiple computers or servers connected into a network. Hardware or software implementations can depend on particular system implementation and constraints. For example, a communication module may include a radio modem, Ethernet module, network interface, communication port, or circuit terminals. In other embodiments, a communication module may include software, software procedure, or software-based function configured to receive and transmit data by a hardware device, such as a processor. Other implementations of communication module can involve programmable and non-programmable microcontrollers, processors, circuits, computing devices, servers, and the like.

The terms "topological data map", "data map", and "graph" shall be construed to mean the same and refer to the visual representation of individual trial subjects or groups of trial subjects by nodes connected with edges.

The terms "trial subject", "study subject", "human subject", and "subject" shall be construed to mean the same and refer to an individual who is the source of data for a research investigator through intervention or interaction with the individual or from individually identifiable information. Such individuals can include healthy humans or patients.

Referring now to the drawings, exemplary embodiments are described. The drawings are schematic illustrations of idealized example embodiments. Thus, the example embodiments discussed herein should not be construed as limited to the particular illustrations presented herein, rather these example embodiments can include deviations and differ from the illustrations presented herein.

FIG. 1 is a block diagram showing an example architecture 100 suitable for implementing methods for topology-based clinical data mining, according to some example embodiments. The architecture 100 may include one or more clinical datasets sources 105, a computer system 110, one or more user computing device(s) 125, and a network 120.

The clinical datasets sources 105 may include server(s) configured to store and provide access to clinical datasets. The clinical datasets can be formatted according to a standard format (for example, a Clinical Data Interchange Standards Consortium (CDISC) format, a Study Data Tabulation Model (SDTM) format, an analysis data model (ADaM) format, and the like).

The computer system 110 may include a standalone server or cloud-based computing resource(s). The standalone server or the cloud-based computing resource(s) can be shared by multiple users. The cloud-based computing resource(s) can include hardware and software available at a remote location and accessible over the network 120. The cloud-based computing resource(s) can be dynamically re-allocated based on demand. The cloud-based computing resources may include one or more server farms/clusters including a collection of computer servers which can be co-located with network switches and/or routers. The computer system 110 may include a system 115 for topology-based clinical data mining.

The one or more user computing device(s) 125 may include a personal computer, a laptop computer, tablet computer, smartphone, server computer, network storage computer, or any other computing device comprising at least networking and data processing capabilities.

The network 120 may include any wired, wireless, or optical networks including, for example, the Internet, intranet, local area network (LAN), Personal Area Network (PAN), Wide Area Network (WAN), Virtual Private Network (VPN), cellular phone networks (e.g., Global System for Mobile (GSM) communications network, packet switching communications network, circuit switching communications network), Bluetooth radio, Ethernet network, an IEEE 802.11-based radio frequency network, a Frame Relay network, Internet Protocol (IP) communications network, or any other data communication network utilizing physical layers, link layer capability, a network layer to carry data packets, or any combinations of the above-listed data networks.

Users of the user computing device(s) 125 may access the system 115 using one or more applications of the client device, for example a web browser, via the network 120. The users may configure the system 115 by selecting clinical datasets and indicating parameters for construction of graphs representing the data in clinical datasets. The system 115 may be further configured to display a graphical representation of the graphs and provide users with a means for selecting groups of trial subjects using the graphical representation. The system 115 may further perform a statistical analysis of predictors of trial subjects within the selected groups. The system 115 may further display the results of statistical analysis.

Figure 2:
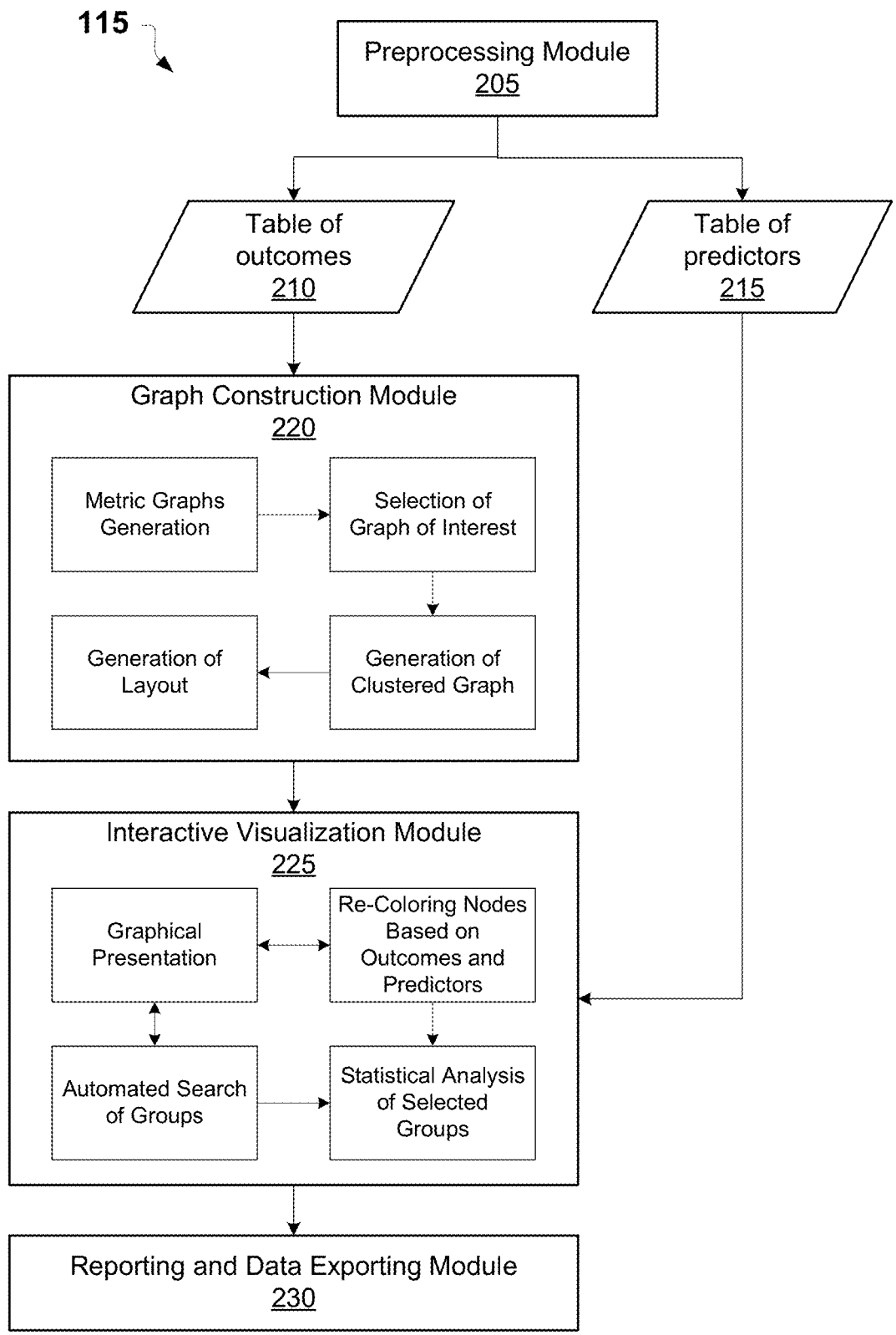
FIG. 2 is a block diagram showing a system for topology-based clinical data mining, according to one example embodiment.

FIG. 2 is a block diagram showing an example system 115 for topology-based clinical data mining, according to some example embodiments. The system 115 may include a preprocessing module 205, a graph construction module 220, an interactive visualization module 225, and a reporting and data exporting module 230.

The preprocessing module 205 may be configured to transform original clinical datasets into a table 210 of outcomes and a table of 215 of predictors. The table 210 may include rows representing trial subjects and columns representing outcomes. The outcomes (also known as response variables) may include biomarkers, results of measurement of vital signs, results of physiological measurements, and questionnaire items recorded during medical treatment of trial subjects. Examples of the outcomes are levels of serum creatinine, blood urea nitrogen, and neutrophil gelatinase-associated lipocalin as a means of evaluating kidney function, absolute or percentage change in the tumor size over the course of study, quality of life score and so forth. The outcome may include questionnaire item to assess trial subject's general health or quality of life, and the like.

The table 215 may include rows corresponding to the trial subjects and predictors associated with the trial subjects. The predictors may include, for example, demographic attributes, such as sex, age, ethnicity, and residence. The predictors may also include medical history attributes and medical interventions attributes.

The clinical datasets can include quantitative data, binary data, or categorical data. The preprocessing module 205 may transform the categorical data into numerical values. For example, an "emotional level" can be represented by numbers of 1 to 7. One of the main problems of clinical datasets is missing values. Therefore, the preprocessing module 205 can be configured to fill in missing values for outcomes in table 210. The preprocessing module 205 can be also configured to combine one or more variables of the clinical data to synthetic variables to aggregate more data for an analysis.

The preprocessing module 205 can be further configured to normalize the values of outcomes to facilitate measurement of distances between data points to find similarities in the clinical datasets. Data points may include row vectors $\{x=(x_1, x_2, \ldots, x_n)\}$, wherein each vector corresponds to a single trial subject x, and $x_i$ denotes the i-th outcome for the trial subject x.

The graph construction module 220 can be configured to generate, based on the table 210 of outcomes, one or more metric graphs (also referred to as "topological data map" or "data map"). In each of the metric graphs, a single node corresponds to an individual trial subject. If two nodes represent similar trial subjects (in terms of pre-defined outcomes), they are connected with an edge. To determine whether two trial subjects are similar, a distance between two data points representing the two trial subjects can be calculated according to a distance function. If the distance does not exceed a distance threshold, then the two nodes (representing the two trial subjects) are connected with an edge.

The construction of a metric graph may depend on a selection of outcomes to be considered when calculating the distance, a distance function to calculate the distance, and a distance threshold. By changing the selection of outcomes, the distance function and the distance threshold, substantial number of metric graphs can be generated.

If the data points represent purely quantitative data, a Euclidean distance, a normalized Euclidean distance, a Manhattan distance, and a Minkowski distance can be used to calculate distances between the data points. A Hamming distance can be used to calculate a distance if the data points represent purely categorical data. If several outcomes of different types (quantitative, binary, categorical) are combined in the table of outcomes, then the data points represent mixed data (quantitative data and categorical data). When the data points represent mixed data, a more general measure of a distance, such as the Gower distance, can be used.

In some embodiments, prior to construction of the metric graphs, the data points $\{x=(x_1, x_2, \ldots, x_n)\}$ can be divided into overlapping subsets. During the construction of the metric graphs, a distance function and distance threshold can be selected independently for each of the overlapping subsets. To obtain the overlapping subsets, each data point $\{x=(x_1, x_2, \ldots, x_n)\}$ is mapped by a projection rule (referred to as a "projection") to the unique point in the set of points $\{p=(p_1, p_2, \ldots, p_m)\}$ (referred to as "the values of the projection" or "projection values"). The projections can be one-dimensional (corresponds to m=1) or multidimensional (corresponding to m>1). The values of the projections can be further divided into overlapping domains. The data points corresponding to one of the overlapping domains can be further collected into one of the overlapping subsets.

The graph construction module 220 can be further configured to select a graph of interest from the metric graphs.

The graph of interest can be determined as the most representative metric graph. To determine the most representative and most stable graph, the graph construction module 220 can calculate values of one or more objective functions of the metric graphs. The objective functions map a set of metric graphs to real numbers. The metric graph having the highest value of one of the objective functions can be selected as the graph of interest. In some embodiments, the objective function may include a projection-driven modularity of the metric graphs. According to some embodiments of the present disclosure, a projection-driven modularity of a metric graph can be defined as a value that measures a difference between the metric graph and a random graph. The difference can be measured within each individual subgraph comprising nodes whose projection values fall into the same domain among the overlapping domains that were used to construct the metric graph.

The graph construction module 220 can be further configured to generate a clustered graph from the graph of interest. In the graph of interest, which is a metric graph, every node corresponds to a single trial subject while two nodes representing trial subjects (in terms of pre-defined outcomes) are connected with an edge. The clustered graph may represent a compressed version of the graph of interest. The compressed version can be obtained using one or more algorithms for clustering of nodes of graphs or community detection in graphs. For example, the compressed version of the graph of interest may include a clustered graph. Unlike the graph of interest (which is a metric graph), each node in the clustered graph corresponds to a group of trial subjects.

The clustering of a metric graph can be based on a modularity of groups of nodes in the metric graph. A cluster can be determined as a group of nodes of the metric graph, wherein the number of edges between nodes within the group is significantly more than the expected number of edges if the edges were distributed randomly within the graph. The modularity reflects a concentration of edges within the cluster in comparison to a random distribution of edges between all nodes in the metric graph according to a statistical model.

The graph construction module 220 can be further configured to generate layouts of the graph of interest in forms of a metric graph and a clustered graph. The layouts can be further used in graphical presentations of the graph of interest. Layout of the nodes of the clustered graph can be visually aligned with a layout of corresponding groups of nodes of the metric graph.

The interactive visualization module 225 can be configured to display a graphical representation of the graph of interest. A user may perform a visual exploration of the graph of interest to discover structural features. In some embodiments, the interactive visualization module 225 may provide a web-based interface for the user. The web-based interface may provide basic operations for visual exploration. The module 225 may display the graphical representation of the graph of interest in the form of a metric graph or a clustered graph based on a user selection. The interactive visualization module 225 may allow zooming in, zooming out, and panning of the graphical representation. The module 225 may provide an additional information for each node using a pop-up window when a user positions a mouse over the node. The module 225 may provide a means for selection of groups of nodes. For example, the module 225 may allow the user to select one or two groups of nodes of the graph of interest. The selected groups can be further used in statistical analysis of predictors associated with trial subjects in the selected groups.

The interactive visualization module 225 may be configured to color the nodes in the graphical representation of the graph of interest. The color of a node can be based on the value of one or more predictors or outcomes of a trial subject that the node represents. The color of a node can be based on a projections value of a data point. A user may re-color the nodes in the graphical representation by selecting a specific outcome or a specific predictor. The color of the nodes may highlight differences between a subgroup of trial subjects represented by a given region of the graphical representation and the rest of the trial subjects participating in a clinical trial, and, thereby, highlight patterns in the clinical datasets. The color of the nodes may also help the user to identify groups of trial subjects to be selected for statistical analysis.

The interactive visualization module 225 may be further configured to perform a statistical analysis of predictors related to trial subjects in the selected groups. In some embodiments, the user can select a region of the graph of interest to specify a group of trial subjects. Then statistical analysis can be performed to find predictors that explain why these trial subjects are combined into a group. After running statistical tests, a table of predictors with their corresponding p-values can be calculated to determine if a distribution of values of the predictors for the selected group of trial subjects is different from a distribution of values of the predictors of the rest of the trial subjects participating in the clinical study.

In some embodiments, the user can select a first region and a second region in the graph of interest, and, thus, select a first group of trial subjects and a second group of trial subjects. The module 225 may further perform calculations of p-values for the statistical tests to determine if a distribution of values of the predictor of the first group of trial subjects is different from a distribution of values of the predictor of the second group of trial subjects.

The interactive visualization module 225 may be also configured to perform an automatic search to highlight a group of related trial subjects in the graph of interest. The automatic search can be performed in addition to the visual inspection of the graph of interest that can be performed by a user. The automatic search can be carried out using machine learning algorithms for automated discovery of groups of trial subjects with common features and similarities.

The reporting and data exporting module 230 can be configured to allow a user to export data for the selected groups of trial subjects and generate one or more reports. The reports may include details of the statistical analysis in the form of a table and charts. The reports can be generated in a portable data format. The data concerning the selected groups of trial subjects may include a table of outcomes and predictors of the trial subjects in the selected group. The data can be exported in comma-separated values or other formats that are acceptable by external statistical analysis platforms. A user may use the exported data to determine other explanatory variables (predictors) that may be responsible for the similarities of responses observed within each selected group of the trial subjects who participated in clinical trial. An additional statistical analysis of the exported data can be performed using SAS™, R, or another data analytics platform.

Figure 3:
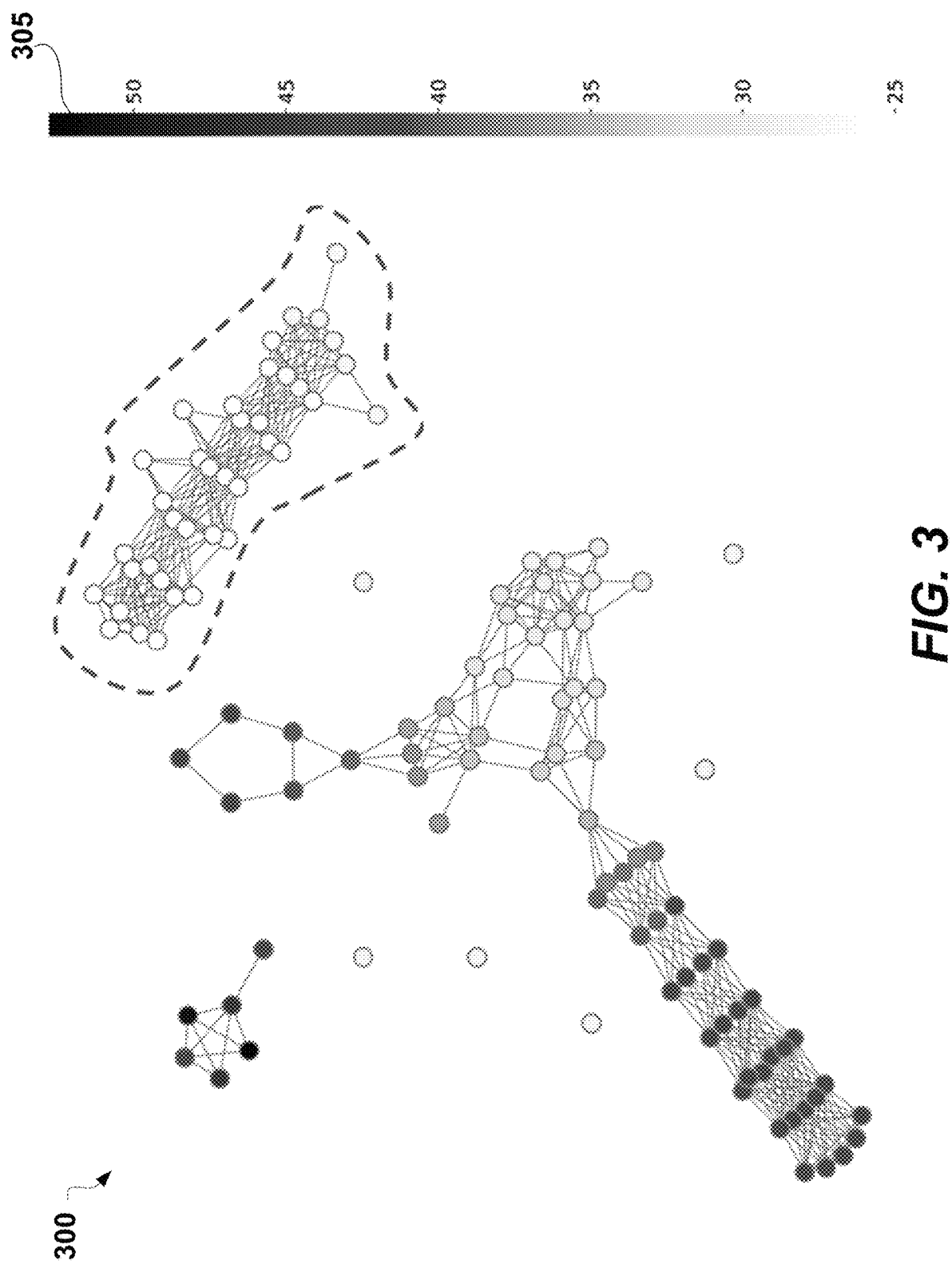
FIG. 3 is a plot of a metric graph, according to an example embodiment.

FIG. 3 shows a plot of an example metric graph 300, according to an example embodiment. Each node of the metric graph 300 represent a trial subject in a table of outcomes used to generate the metric graph. The nodes of the metric graph 300 are selectively connected. The nodes of the metric graph 300 are colored based on the value of a selected outcome or a selected predictor 305. Any group of the nodes can be selected for performing a statistical analysis of the predictors of the trial subjects within the groups.

Figure 4:
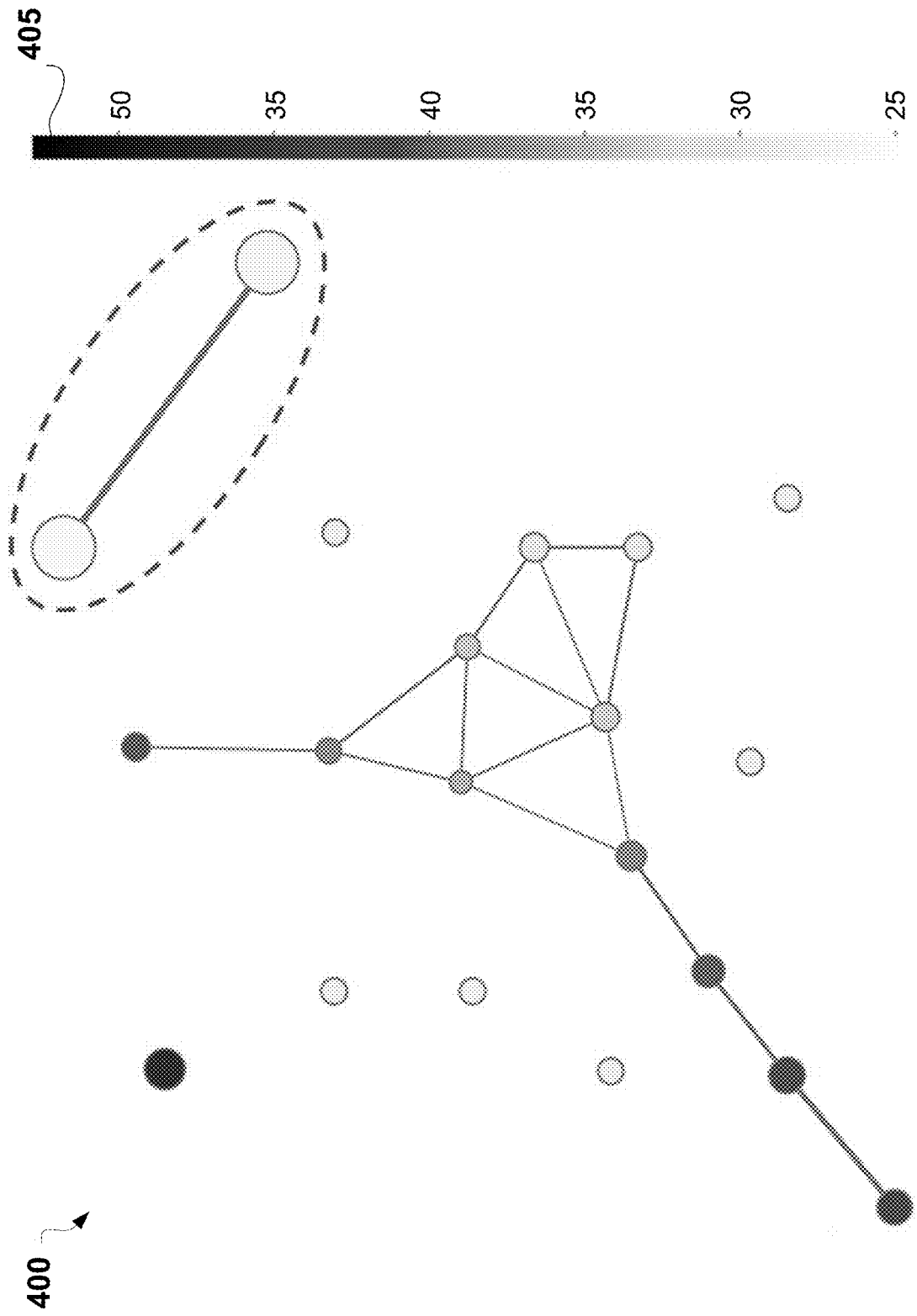
FIG. 4 is a plot of a clustered graph, according to an example embodiment.

FIG. 4 is a plot of a clustered graph 400, according to an example embodiment. Each node in the clustered graph 400 corresponds to a cluster of nodes in a metric graph. The color of a node in the clustered graph 400 can be based on a mean of values of a selected outcome or a selected predictor 405 for the trial subjects within the node.

Figure 5:
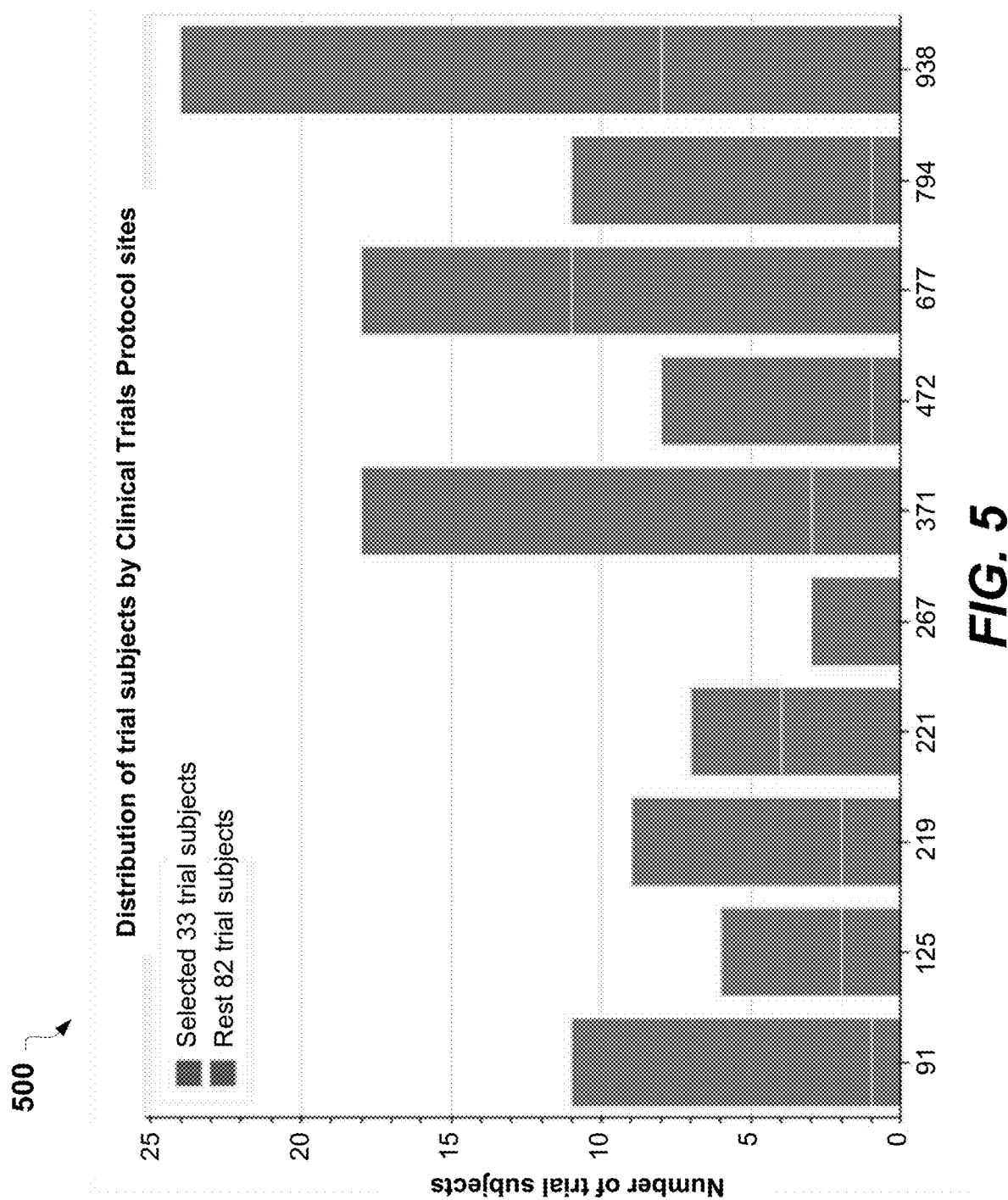
FIG. 5 is a chart diagram of distribution of trial subjects by a selected predictor for a selected group of trial subjects versus the rest of the trial subjects within clinical datasets, according to an example embodiment.

FIG. 5 is bar chart 500 of a distribution of trial subjects by a selected predictor for a selected group of trial subjects versus the rest of trial subjects, according to an example embodiment. In the example of FIG. 5, the selected predictor is the site at which clinical datasets are collected. Trial subjects from the selected group prevail in site 221 and site 677 while other clinical study sites exhibit the opposite pattern. This pattern may indicate that the distribution of trial subjects at site 221 and site 677 may result from, for example, a violation of a procedure for selecting of individuals to participate in the study, or a violation of a protocol of data collection for the individuals assigned to site 221 and site 677.

Figure 6:
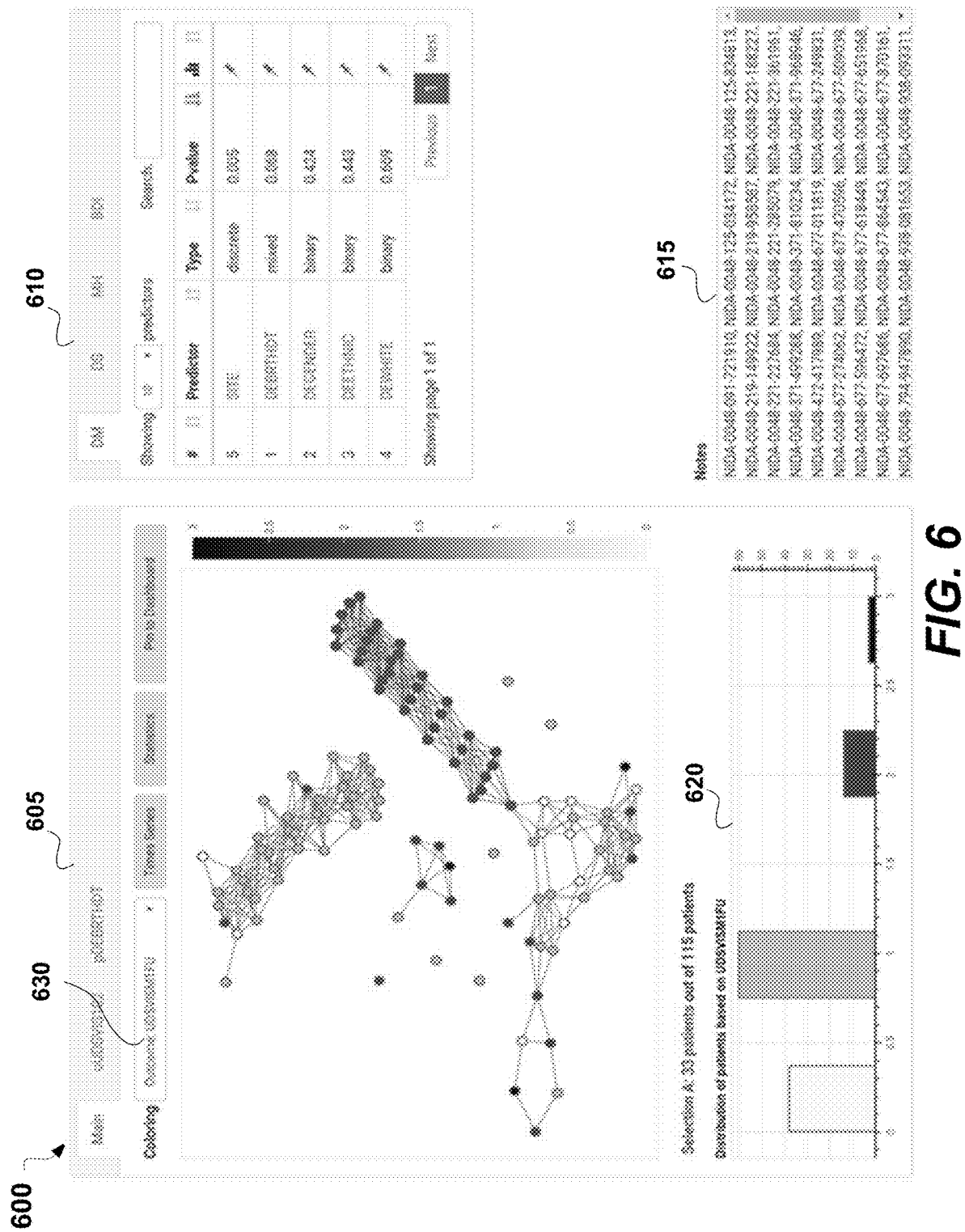
FIG. 6 shows a screen of an interactive visualization module, according to an example embodiment.

FIG. 6 shows a screen 600 of an interactive visualization module 225, according to an example embodiment. The screen 600 may include a window 605 showing a graphical presentation of a graph of interest in the form of a metric graph. Each node of the metric graph represents a single trial subject. The interactive visualization module 225 may allow a user to select a group of trial subjects in the graphical presentation. The nodes of the metric graphs are colored based on a value of an outcome selected in the field 630. The screen 600 may also include a plot 620 showing a distribution of trial subjects based on the value of an outcome or a predictor that was selected in the field 630.

The screen 600 may further include a table 610. The table 610 includes p-values for the statistical tests calculated to determine whether a distribution of values of the predictor for the trial subjects within selected group is different from a distribution of values for the predictor for the rest of trial subjects. In the example of FIG. 6, the predictors include a site at which clinical data are collected, birth date of a trial subject, gender of the trial subject, and ethnicity of the trial subject. The screen 600 may also show table 615 illustrating data related to the nodes of the metric graph displayed in window 605.

FIG. 7 is a process flow diagram showing a method 700 for topology-based clinical data mining, according to an example embodiment. The method 700 may be performed by processing logic that comprises hardware (e.g., decision-making logic, dedicated logic, programmable logic, ASIC, and microcode), software (such as software run on a general-purpose computer system or a dedicated machine), or a combination of both. The method 700 may have additional operations not shown herein, but which can be evident to those skilled in the art from the present disclosure. The method 700 may also have fewer operations than outlined below and shown in FIG. 7.

The method 700 may commence in block 705 with processing, by a pre-processing module, the clinical datasets to generate a first table and a second table. The first table may include first rows representing trial subjects and first columns including outcomes of the trial subjects. The second table may include second rows representing the trial subjects and second columns including predictors of the trial subjects. The outcomes may include biomarkers, vital signs, results of physiological measurements, and questionnaire items. The predictors may include one or more of demographic attributes, medical history attributes, and medical interventions attributes. The processing of the clinical datasets may include normalizing data in the clinical datasets, filling in missing values for the outcomes in the first table. The processing may include generating synthetic variables based on the data clinical datasets. The synthetic variables can represent a combination of one or more outcomes associated with trial subjects.

In block 710, the method 700 may generate, by a graph construction module and based on the first table, one or more metric graphs. The metric graphs include nodes and edges. The nodes represent the trial subjects and the edges selectively connect the nodes according to one or more pre-determined criteria. For example, the method 700 may calculate a distance between a first data point and a second data point. The first data point is a first vector $(x_1, x_2, \ldots, x_n)$ of outcomes of a first trial subject x represented by a first node. The second data point is a vector $(y_1, y_2, \ldots, y_n)$ of outcomes of a second trial subject y represented by a second node. The distance can be determined by a Euclidean distance, a normalized Euclidean distance, a Minkowski distance, a Manhattan distance, a Hamming distance, or a Gower distance. The method 700 may determine that the distance is below a pre-determined value. Based on the determination, the method 700 may selectively connect the first node and the second node by an edge. A set of the metric graphs can be received by varying at least a selection of outcomes used to calculate the distance, distance function, and the distance threshold.

In block 715, the method 700 may select, by the graph construction module, a graph of interest from the one or more metric graphs. For example, the method 700 may determine a highest project-driven modularity graph from the one or more metric graphs and select the highest project-driven modularity graph as the graph of interest.

In block 720, the method 700 may generate, by the graph construction module, a compressed version of the graph of interest. The compressed version may include a clustered graph generated based on the graph of interest. The clustered graph may include one or more nodes, wherein the nodes represent groups of the trial subjects.

In block 725, the method 700 may generate, by the graph construction module, a first layout of the graph of interest and a second layout of the compressed version of graph of interest. The first layout and the second layout can be visually aligned during the generation.

In block 730, the method 700 may display, by an interactive visualization module and based on the first layout or the second layout, a graphical representation of the graph of interest.

In block 735, the method 700 may assign, by the interactive module, colors to the nodes of the graph of interest. The colors of the nodes can be based on a selected outcome or a selected predictor. The method 700 may receive the selected outcome or the selected predictor based on an user input via the interactive visualization module. The colors can be determined by values for the selected predictor or the selected outcome for the trial subjects corresponding to the nodes. Prior to selection of a predictor or an outcome, the colors of the nodes can be assigned based on projection values of data points, wherein the data points are vectors of outcomes of trial subjects corresponding to the nodes.

In block 740, the method 700 may perform, by the interactive module, an automatic search to identify at least one group of related trial subjects (in terms of pre-defined outcomes). The automatic search can be performed using one or more machine learning algorithms.

In block 745, the method 700 may highlight, by the interactive module, nodes corresponding to the related trial subjects in the graphical representation.

In block 750, the method 700 may receive a user input by the interactive visualization module and via the graphical representation. The user input may include one or more selected groups of the trial subjects. nodes In block 755, the method 700 may perform, by the interactive visualization module configured to use the second table, a statistical analysis of predictors associated with trial subjects within the one or more selected groups of the trial subjects. The statistical analysis may include calculating p-values for the statistical tests to determine whether a distribution of the predictor values of trial subjects within a first group from the one or more selected groups is different from a distribution of the predictor values for the trial subjects within a second group from the one or more selected groups. The statistical analysis may include calculating p-values for the statistical tests to determine whether a distribution of the predictor values for the trial subjects within one of the selected groups is different from a distribution of the predictor values for the rest of trial subjects.

In block 760, the method 700 may display, by the interactive visualization module, results of the statistical analysis. The result can be displayed in the form of a table of p-values for the predictors and in form of bar charts or histograms showing distribution of the predictors.

Figure 8:
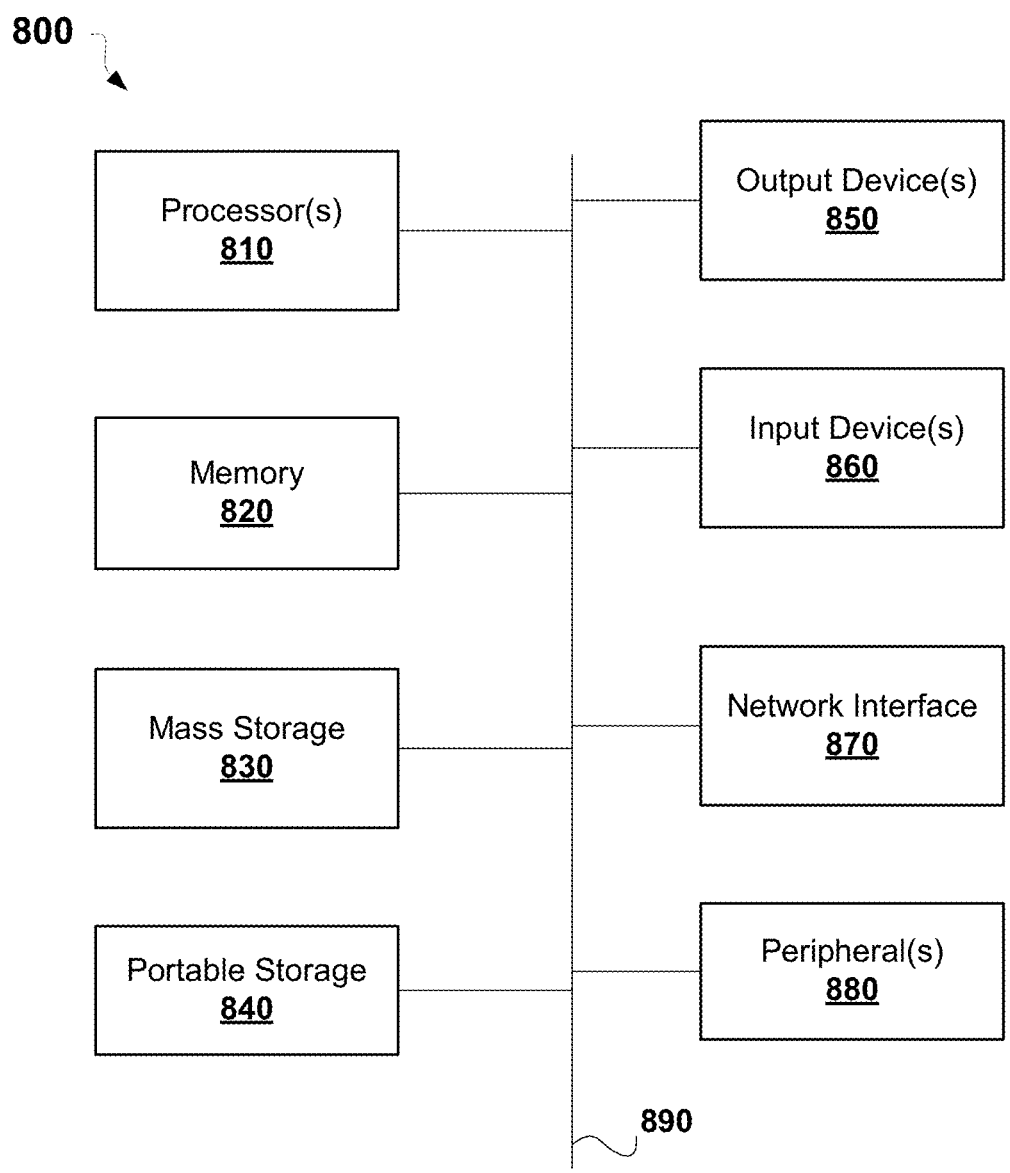
FIG. 8 is a computer system that can be used to implement the methods for topology-based clinical data mining as described herein.

FIG. 8 is a block diagram illustrating an example computer system 800 suitable for implementing the methods described herein. In particular, computer system 800 may be an instance of computer system 110, clinical datasets sources 105, or user computing device(s) 125. FIG. 8 illustrates just one example of computer system 800 and, in some embodiments, computer system 800 may have fewer components than shown in FIG. 8 or more components than shown in FIG. 8.

Computer system 800 includes one or more processors 810, a memory 820, one or more storage devices 830, a portable storage 840, one or more input devices 860, one or more output devices 850, network interface 870, and one or more peripherals 880. These components can be operatively interconnected via a communication bus 890. Processors 810 are, in some examples, configured to implement functionality and/or process instructions for execution within computer system 800. For example, processors 810 may process instructions stored in memory 820 or instructions stored on storage devices 830. Such instructions may include components of an operating system or software applications.

Memory 820, according to one example, is configured to store information within computer system 800 during operation. Memory 820, in some example embodiments, may refer to a non-transitory computer-readable storage medium or a computer-readable storage device. In some examples, memory 820 is a temporary memory, meaning that a primary purpose of memory 820 may not be long-term storage. Memory 820 may also refer to a volatile memory, meaning that memory 820 does not maintain stored contents when memory 820 is not receiving power. Examples of volatile memories include RAM, dynamic random access memories (DRAM), static random access memories (SRAM), and other forms of volatile memories known in the art. In some examples, memory 820 is used to store program instructions for execution by the processors 810. Memory 820, in one example, is used by software. Generally, software refers to software applications suitable for implementing at least some operations of the methods as described herein.

Storage devices 830 can also include one or more transitory or non-transitory computer-readable storage media and/or computer-readable storage devices. In some embodiments, storage devices 830 may be configured to store greater amounts of information than memory 820. Storage devices 830 may further be configured for long-term storage of information. In some examples, the storage devices 830 include non-volatile storage components. Examples of such non-volatile storage components include magnetic hard discs, optical discs, solid-state discs, flash memories, forms of electrically programmable memories (EPROM) or electrically erasable and programmable memories, and other forms of non-volatile memories known in the art.

Still referencing to FIG. 8, computer system 800 may also include one or more input devices 860. Input devices 860 may be configured to receive input from a user through tactile, audio, video, or biometric channels. Examples of input devices 860 may include a keyboard, keypad, mouse, trackball, touchscreen, touchpad, microphone, one or more video cameras, image sensors, fingerprint sensors, or any other device capable of detecting an input from a user or other source and relaying the input to computer system 800 or components thereof. As such, input devices 860 can be used by users or operators of system 105 to input commands, instructions, data, settings, and the like.

Output devices 850, in some examples, may be configured to provide output to a user through visual or auditory channels. Output devices 850 may include a video graphics adapter card, a liquid crystal display (LCD) monitor, a light emitting diode (LED) monitor, an organic LED monitor, a sound card, a speaker, a lighting device, a LED, a projector, or any other device capable of generating output that may be intelligible to a user. Output devices 850 may also include a touchscreen, presence-sensitive display, or other input/output capable displays known in the art. Accordingly, output devices 850 can be used to output customized reports generated by system 105.

Computer system 800, in some example embodiments, also includes network interface 870. Network interface 870 can be utilized to communicate with external devices via one or more networks such as one or more wired, wireless, or optical networks including, for example, the Internet, intranet, local area network, wide area network, cellular phone networks (e.g. GSM communications network, packet switching communications network, circuit switching communications network), Bluetooth radio, and an IEEE 802.11-based radio frequency network, among others. Network interface 870 may be a network interface card, such as an Ethernet card, an optical transceiver, a radio frequency transceiver, or any other type of device that can send and receive information.

An operating system of computer system 800 may control one or more functionalities of computer system 800 or components thereof. For example, the operating system of computer system 800 may interact with software applications of computer system 800 and may facilitate one or more interactions between the software applications and one or more of processors 810, memory 820, storage devices 830, input devices 860, and output devices 850. The operating system of computer system 800 may interact with the software applications and components thereof. In some embodiments, the software applications may be included in the operating system of computer system 800. In these and other examples, virtual modules, firmware, or software of the software applications. In other examples, virtual modules, firmware, or software may be implemented externally to computer system 800, such as at a network location. In some such instances, computer system 800 may use network interface 870 to access and implement functionalities provided by virtual modules, firmware, or software for vehicle identification through methods commonly known as "cloud computing."

Figure 9:
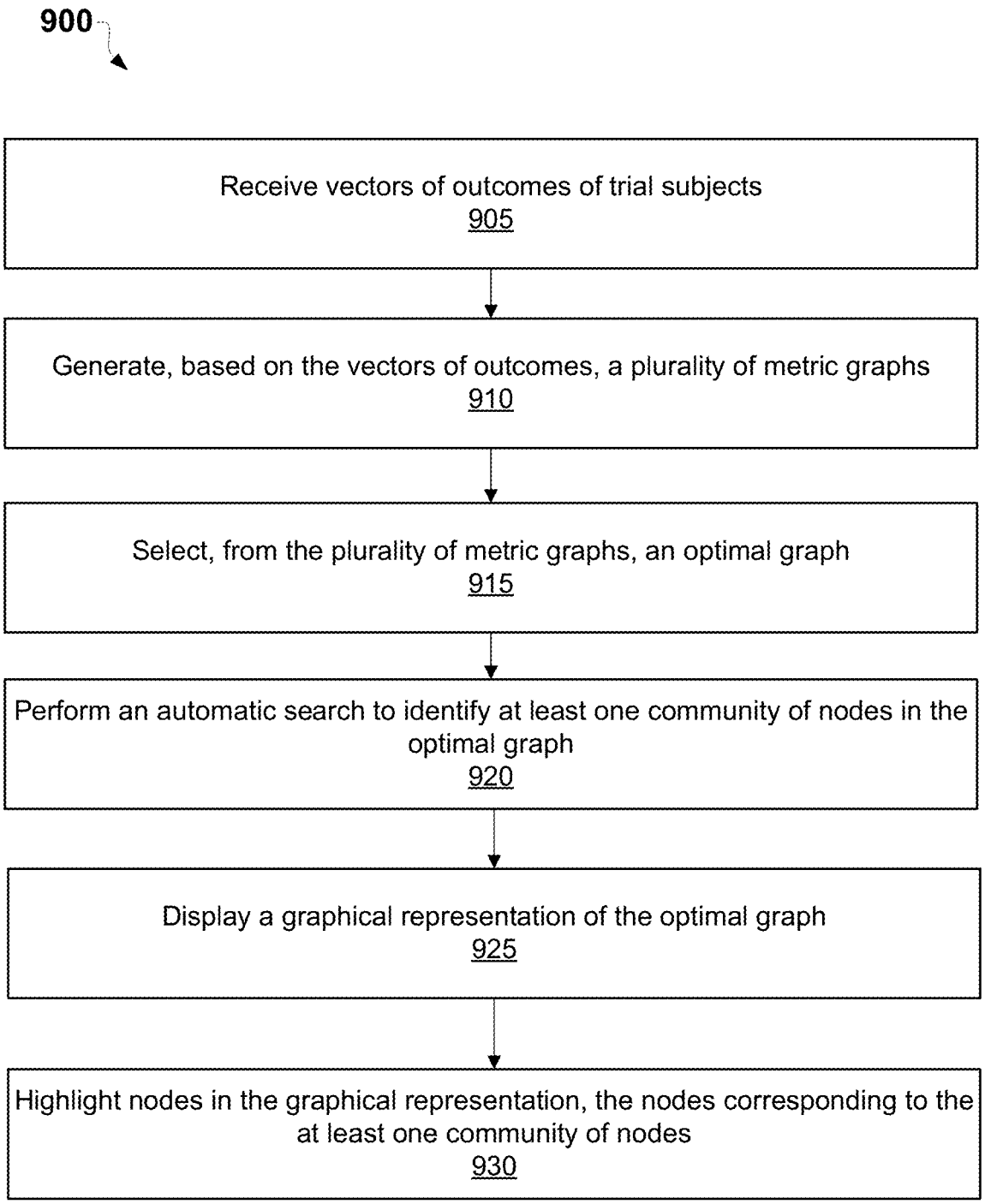
FIG. 9 is a flow chart showing a method for graph-based discovery of geometry of clinical data, according to an example embodiment.

FIG. 9 is a flow chart showing a method 900 for graph-based discovery of geometry of clinical data, according to some example embodiment. The method 900 may be performed by processing logic that comprises hardware (e.g., decision-making logic, dedicated logic, programmable logic, ASIC, and microcode), software (such as software run on a general-purpose computer system or a dedicated machine), or a combination of both. The method 900 may include additional operations not shown herein, but which can be evident to those skilled in the art from the present disclosure. The method 900 may also have fewer operations than outlined below and shown in FIG. 9.

The method 900 may commence in block 905 with receiving vectors of outcomes of trial subjects: $\{s(k)=(s_1(k), s_2(k), \ldots, s_n(k))\}$, where $s_i(k)$ denotes the i-th outcome for k-th trial subject.

In block 910, the method 900 may include generating, based on the vectors of outcomes, a plurality of metric graphs. Each of the metric graphs may include a set of nodes and a set of edges. Each node of the set of nodes may correspond to one of the vectors of outcomes s(k). Generating the set of edges is detailed in FIG. 10.

In block 915, the method 900 may include selecting, from the plurality of metric graphs, a graph of interest (also referred to as an optimal graph). In some embodiments, the optimal graph can be determined based on modularity, which is a value that measures how similar a metric graph is to a random graph. The random graph can be constructed using the same set of nodes as the metric graphs in the plurality of metric graphs. A metric graph having the largest value of modularity can be selected as the optimal graph because such metric graph is the least similar to the random graph.

In some other embodiments, the optimal graph can be determined using the Kolmogorov complexity. The Kolmogorov complexity is a value that measures an amount of information encoded in an incidence matrix of the vertices of the optimal graph. Because each of the metric graphs can be encoded using an incidence matrix of the vertices, an amount of information can be determined for each of the metric graphs. A metric graph corresponding to an incident matrix encoding the largest amount of information can be selected as the optimal graph.

In yet other embodiments, the optimal graph can be determined using the Gromov-Hausdorff distance. In these embodiments, it is assumed that each of the metric graphs can define a metric space. The Gromov-Hausdorff distance is a metric that measures the distance between metric spaces. In these embodiments, selecting the optimal graph may include calculating Gromov-Hausdorff distances between each of the metric graphs and a dull graph. The dull graph can be defined as the most non-informative metric graph that can be built using the set of nodes which is common for the metric graphs. The construction of the dull graph can be based on coverings (also referred to as overlapping domains) of projections of vectors of data points obtained from vectors of outcomes. The construction of coverings is described in more detail below with regard to FIGS. 10 and 11. The dull graph can be constructed by connecting the nodes if the nodes correspond to vectors of outcomes belonging to the same overlapping domain. Thus, all nodes corresponding to the same overlapping domain are connected to each other. Dull graphs obtained for each of the overlapping domains can be combined into one common dull graph. After the dull graph is constructed, the Gromov-Hausdorff distances between the metric graphs and the dull graph can be computed. A metric graph having the largest distance from the dull graph can be selected as the optimal graph. As described below, the plurality of metric graphs can be constructed by varying parameters for constructing a metric graph. In some embodiments, a dull graph can be constructed for each selection of the parameters. Thus, each metric graph from the plurality of metric graphs can be associated with an individual dull graph obtained with the same parameters as the metric graph. Thus, each metric graph from the plurality of metric graphs can be compared to its corresponding dull graph. In these embodiments, the Gromov-Hausdorff distances can be calculated between the metric graph and the dull graph corresponding to this metric graph. A metric graph having the largest distance from the dull graph corresponding to the metric graph can be selected as the optimal graph.

In block 920, the method 900 may include performing an automatic search to identify communities of nodes in the optimal graph. A community can be determined as a dense conglomeration of nodes in the optimal graphs. The dense conglomeration can be determined as a subset of the nodes, where all or most of nodes are connected with each other. The community can be a subset of nodes with a higher or denser level of connectivity of nodes between each other as compared to the level of connectivity of the nodes outside this subset. The community may represent a subset of trial subjects that can be compared with all the others trial subjects to determine one or more statistical dependences in outcomes and predictors.

In some example embodiments, the communities can be determined using a machine learning using betweenness, modularity, and other properties of the subset of the nodes. In other embodiments, the communities can be determined using a clique percolation method. The clique percolation method includes determining a data pattern of connections between the nodes using a parameter. The parameter may indicate a number of nodes that are fully connected to each other. The community can be determined as an area in the optimal graph, where the same data pattern occurs a predetermined number of times. In some embodiments, the communities can be selected, using the parameter, in such a way that the communities do not overlap and the number of nodes that do not belong to the selected communities does not exceed a certain threshold. The threshold can be selected based on features of the clinical datasets (e.g., outcomes) and the structure of the graph. In block 925, the method 900 may include displaying a graphical representation of the optimal graph. In block 930, the method 900 may include highlighting those nodes in the graphical representation that belong to the community of nodes.

Figure 10:
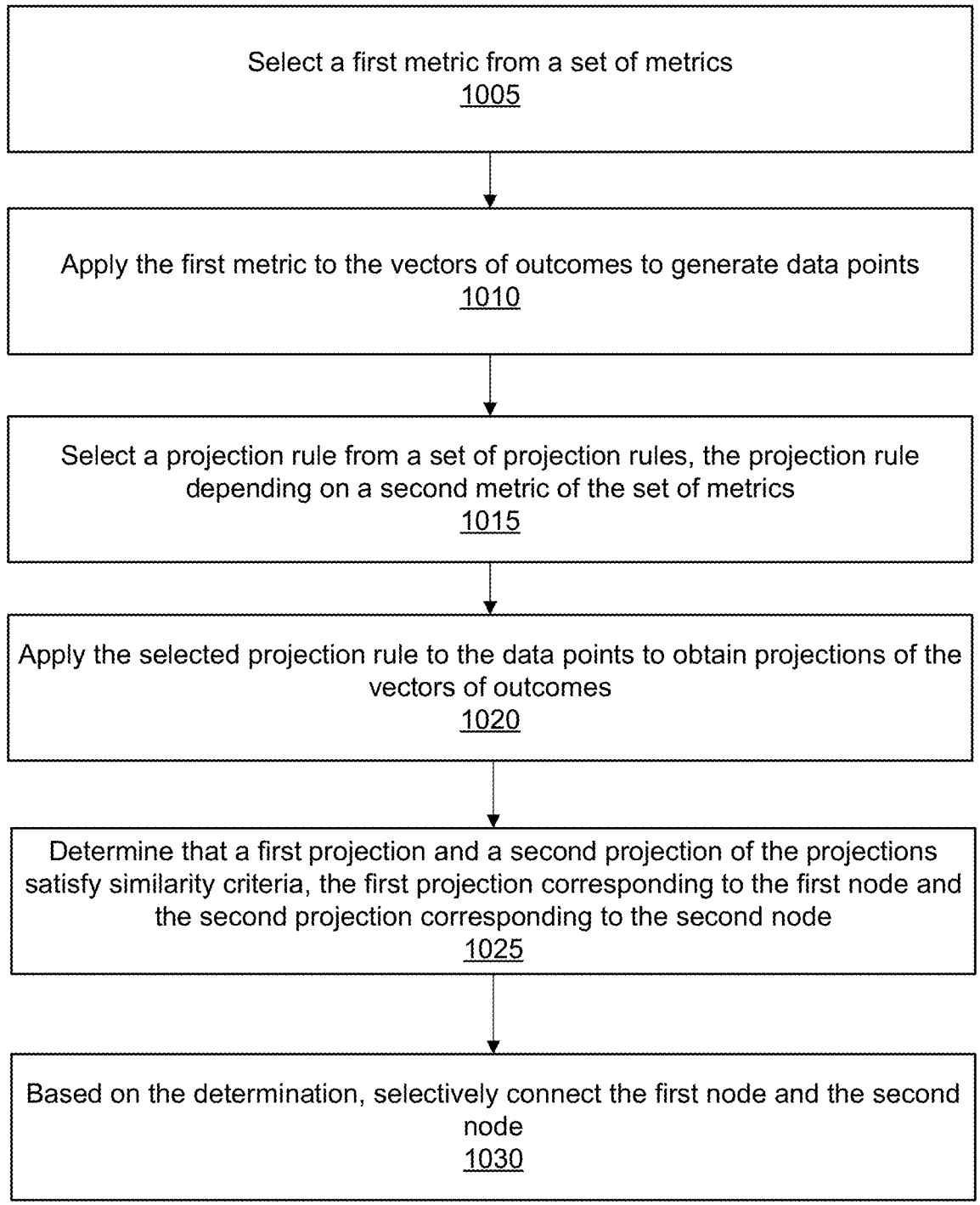
FIG. 10 is a flow chart showing a method for generating edges in a metric graph, according to various example embodiments.

FIG. 10 is a flow chart showing a method 1000 for generating edges in a metric graph, according to various example embodiments. The method 1000 may provide details for the block 910 of the method 900 shown in FIG. 9.

The method 1000 may commence with transforming $\{s(k)=(s_1(k), s_2(k), \ldots, s_n(k))\}$ to generate data points $\{x(k)=(x_1(k), x_2(k), \ldots, x_n(k))\}$ in blocks 1005 and 1010. In block 1005, the method 1000 may include selecting a first metric from a set of metrics. The set of metrics may include a Minkowski distance, a normalized Euclidean distance, a Hamming distance, a Gower distance, and other metrics. The Minkowski distance is defined by the following formula:

$$d(x, y) = \left(\sum_{i=1}^{n} |x_i - y_i|\right)^{\frac{1}{p}}$$

and can be used with parameter p=1 (Manhattan distance), p=2 (Euclidean distance), or other parameters of p.

In block 1010, the method 1000 may include applying the first metric to the vectors of outcomes $\{s(k)=(s_1(k), s_2(k), \ldots, s_n(k))\}$ to generate data points $\{x(k)=(x_1(k), x_2(k), \ldots, x_n(k))\}$. If the outcomes are heterogeneous, that is the components $s_1(k), s_2(k), \ldots, s_n(k))$ are measured in different units and are of different size, then the data points $\{x(k)=(x_1(k), x_2(k), \ldots, x_n(k))\}$ can be normalized. The normalization may include standard scaling, robust scaling, or minmax scaling. The standard scaling can be performed by subtracting the mean value from the components and scaling the components to unit dispersion. The standard scaling can be implemented by introducing weight coefficients in the Minkowski metric, where the weight coefficients are equal to the inverse standard deviations.

The robust scaling includes determining a median and an interquartile range for each of the components of vectors of outcomes. The scaling of the components of vectors of outcomes includes dividing the components by the interquartile ranges. The minmax scaling includes determining a minimum and a maximum for each the components of vectors of outcomes. The scaling of the components of vectors of outcomes includes dividing the components by the difference between the maximum and the minimum.

The standard scaling can be applied to vectors of outcomes with components having a distribution close to the standard distribution. The robust scaling and minmax scaling can be applied to vectors of outcomes including mixed data, that is including binary data, categorical data, and numeric data.

In other embodiments, a cosine metric can be used for the vectors of outcomes including text data. If components of the vector of outcomes include time series, then distance metric between two time series can be determined using dynamic time wrapping (DTW) or minimum jump cost (MJC).

In some embodiments, the set of metrics may include a complex metric. The complex metric may include a weighted sum of metrics determined based on subsets of components of the vectors of outcomes. A metric can be individually selected for each of subsets of components to construct a distance matrix for this subset. If the subsets are heterogeneous, that is the outcomes belonging to different subsets are measured in different units, the distance matrices for the subset can be normalized and summed up. The normalization can be carried out to balance the contribution of each of the subset to the overall result. The normalization may include dividing the distance matrix for each of the subsets by a scale. The scale can be chosen as a standard deviation of the distance matrix, an interquartile range of the distance matrix, or maximum value in the distance matrix.

If the subsets of components of vectors of outcomes are homogeneous, that is the outcomes in the subsets are measured in the same units, then the normalization can be omitted. The normalization can be also omitted if the metrics selected to construct the distance matrices for the subsets include normalization. These metrics may include Hamming distance, Jaccard distance, or correlation.

The resulting distance matrix can be determined as a weighted sum of distance matrices determined for the subsets. The weights can be determined based on numbers of components in subsets, number of the subsets, and based on user input indicating significance of the components for solving a specific problem.

In one example, the outcomes may have a tree structure, that is outcomes can be detailed by a group of features, which, in turn, can be detailed by further features (also referred to as subfeatures), and so on. To equalize the contribution of subfeatures in the metric measuring the distance between vectors of outcomes, the distances can be calculated first on groups of subfeatures. Then the resulting metric can be determined as a weighted sum of the distances calculated on groups of subfeatures. Weight coefficients in the sum can be equal to reciprocals of sizes of subsets corresponding to subfeatures.

In embodiments with outcomes including time series, a combined metric can be used to determine distances between the vectors of outcomes. For example, if the outcomes include one or more concurring time series, then the combined metric can be obtained by combining metrics for each of the concurring time series. If the time series are not synchronized, then the DTW or the MJC can be used for calculating the distances between the time series. If the synchronization and the number of events in the time series are the same, one of the standard metrics for vector rows (Euclidean, Minkoswki, and so forth) can be used for determining the distances between the time series. Prior to using the standard metrics, a sliding window averaging the time series can be used to reduce noise and dimensionality of data in the time series. The size of the sliding window can be selected based on the specifics of data.

In block 1015, the method 1000 may include selecting a projection rule from a set of projection rules. The projection rule can depend on a second metric of the set of metrics.

In block 1020, the method 1000 may include applying the selected projection rule to the data points $\{x(k)=(x_1(k), x_2(k), \ldots, x_n(k))\}$ to obtain projections $\{p(k)=(p_1(k), p_2(k), \ldots, p_m(k))\}$ of the vectors of outcomes. The set of projection rules may include geometric projections, such as Principal Component Analysis (PCA), Multidimensional Scaling (MDS), t-distributed Stochastic Neighbor Embedding (tSNE), and others. The dimension m of projections can be less or equal to the dimension n of the data points.

The set of projection rules may include a density projection, which is useful for determining density of data points and discovery of dense clusters of the data points. The dimension m of the density projection is 1. The density projection can be determined by the following formula:

$$p_1(x) = \sum_{i=1}^{N} \exp\left(\frac{-d(x, x_i)^2}{2\sigma^2}\right)$$

where $\sigma$ is density parameter, d is the second metric, which can be the same or different than the first metric, and N is the total number of trial subjects in the dataset.

The set of projection rules may include a centrality projection, which depends on a parameter s, $1 \leq s < +\infty$ and can be determined by the formula:

$$p_2(x) = \left(\frac{\sum_{i=1}^{N} d(x, x_i)^s}{N}\right)^{1/s}$$

If $s = +\infty$, then $p_2(x) = \max_{i=1,2,\ldots,N} d(x, x_i)$, where x is a subject trial, d is the second metric that can be the same or different than the first metric. The centrality projection can be used for discovery of outliers.

The set of projection rules may include a data driven projection. The data driven projection can be used for analyzing stratification of outcomes using features taken from predictors. The dimension m of the data driven projection may not depend on the dimension n of data points. The dimension m of the driven projection can depend on a number of predictors.

The set of projection rules may include multidimensional projections. The multidimensional projections can be constructed as a combination of one-dimensional projections. For example, the set of projection rules may include a two-dimensional projection obtained as a combination of the centrality and density projections. Different projection rules in the set of projection rules can be constructed by selecting different geometrical projections, different parameter s of the centrality projection, different parameter $\sigma$ of the density projection, different metric d in formulas of the centrality projection and the density projection, different multidimensional combinations of geometrical projections, the density projection, and the centrality projection. Each of the different projection rules can be further used to construct edges in the set of nodes to obtain different metric graphs in the plurality of the metric graphs.

Operations of the following blocks 1025 and 1030 of the method 1000 can be performed for each of a first node and a second node of the set of nodes. In block 1025, the method 1000 may determine that a first projection and a second projection of the projections satisfy similarity criteria, where the first projection corresponds to the first node and the second projection corresponds to the second node.

In block 1030, the method 1000 may selectively connect, based on the determination that the first projection and the second projection satisfy similarity criteria, the first node and the second node. Determining that the first projection and the second projection satisfy the similarity criteria may include determining that the first projection and the second projection are located within the same domain in a set of overlapping domains and belong to the same cluster in a tree of clusters. The tree of clusters can be generated based on all projection belonging to the same domain and by varying a level of granularity. The first node and the second node can be connected if the first projection and the second projection belong to a cluster obtained with an optimal level of granularity obtained for the domain.

Figure 11:
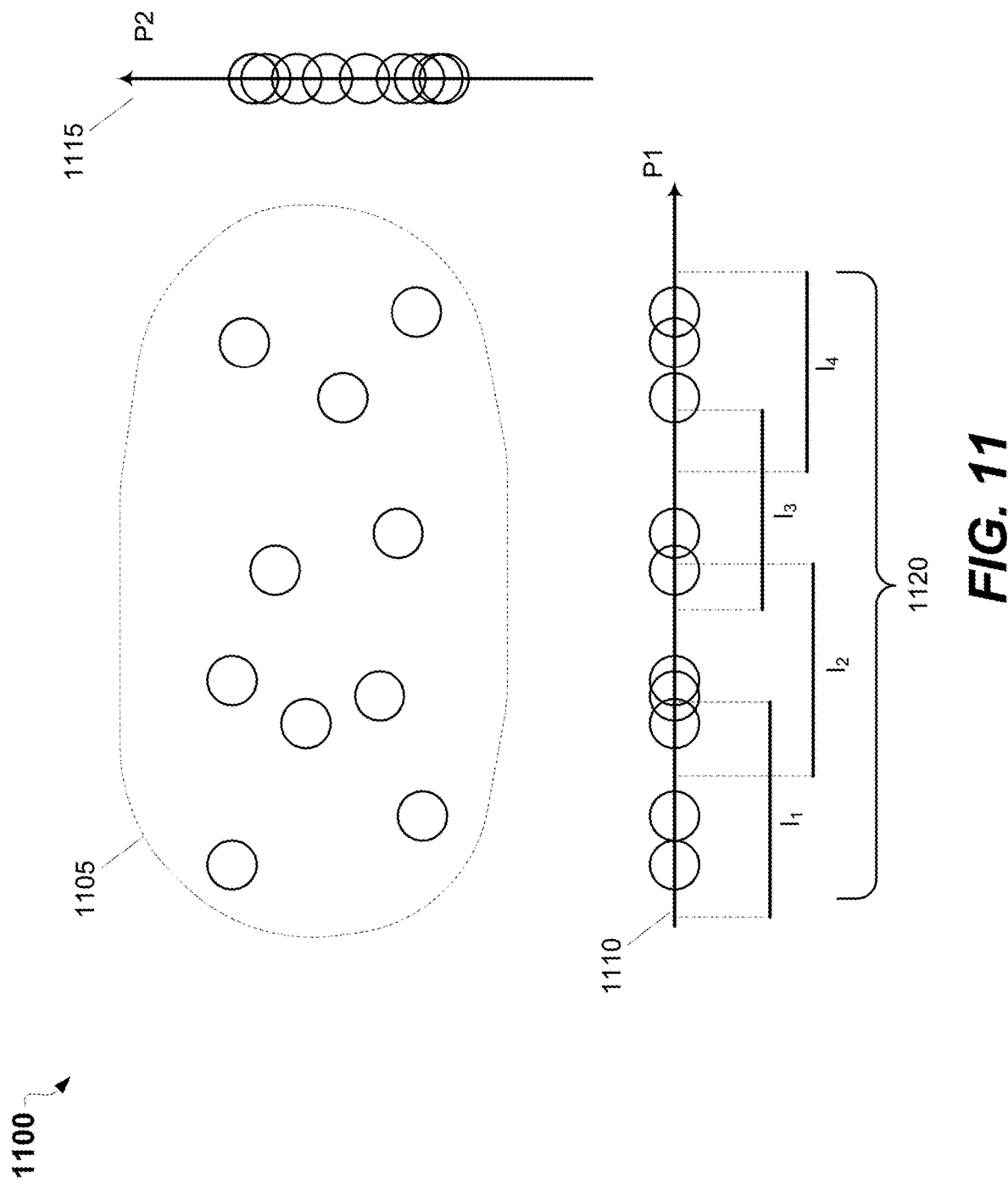
FIG. 11 is a schematic diagram showing data points, projections of data points, and overlapping domains covering the projections, according to an example embodiment.

FIG. 11 is schematic diagram 1100 showing data points 1105, projections 1110, projections 1115, and overlapping domains 1120, according to an example embodiment. The overlapping domains $I_l$ may be constructed by calculating range for each of the projections as an interval between maximal and minimum component $p_i$ in $\{(p_1(k), p_2(k), \ldots, p_m(k))\}$. Then the range can be covered by $q_i$ overlapping domains $I_l$, $l=1, \ldots, q_i$ and selecting a percentage of overlapping. The interval $I_i$ overlaps the interval $I_j$ with percentage $o_{ij}$ of overlapping if the length of interval $I_i \cap I_j$ is $o_{ij}$ percent of the length of interval $I_j$. It should be noted that, in general, $o_{ij} \neq o_{ji}$. In some embodiments, the overlap parameter can be the same for all pairs of overlapping intervals. In certain embodiments, the overlap parameter is 50 percent. Larger overlap parameters result in obtaining the metric graphs having more connected nodes, which is preferable. The number of overlapping domains ($q_i$) can be selected such that the number of projections of data points from the source dataset falling into a single overlapping domain (interval) is within a predetermined limit. In certain embodiments, the predetermined limit is 1000.

A uniform covering can be used if the distribution of the projections is close to a uniform distribution. The uniform covering is a covering with the entire range being covered by intervals of equal length. In this case, each overlapping interval may contain a different number of points.

A balanced covering can be used if the distribution of projection values is extremely uneven. A balanced covering is a covering with overlapping intervals containing an approximately equal number of projections.

In both cases, the boundaries of overlapping intervals can be determined by the number of the intervals and percentage of overlapping. The selection of the number of the intervals and the percentage of overlapping for uniform covering may result in an unambiguous coverage. The selection of the number of the intervals and the percentage of overlapping for the balanced covering may result in different coverings. However, using different balanced coverings does not affect the structure of the graph.

Multidimensional overlapping domains can be obtained as the Cartesian product of two and more one-dimensional coverages. A $(k_1, k_2, \ldots k_m)$ multidimensional domain may include points that lie simultaneously in the $k_1$-th domain of the first one-dimensional coverage, the $k_2$-th of the second one-dimensional coverage, and so forth. In other embodiments, multidimensional overlapping domains can be different from the Cartesian products of one-dimensional domains.

Figure 12:
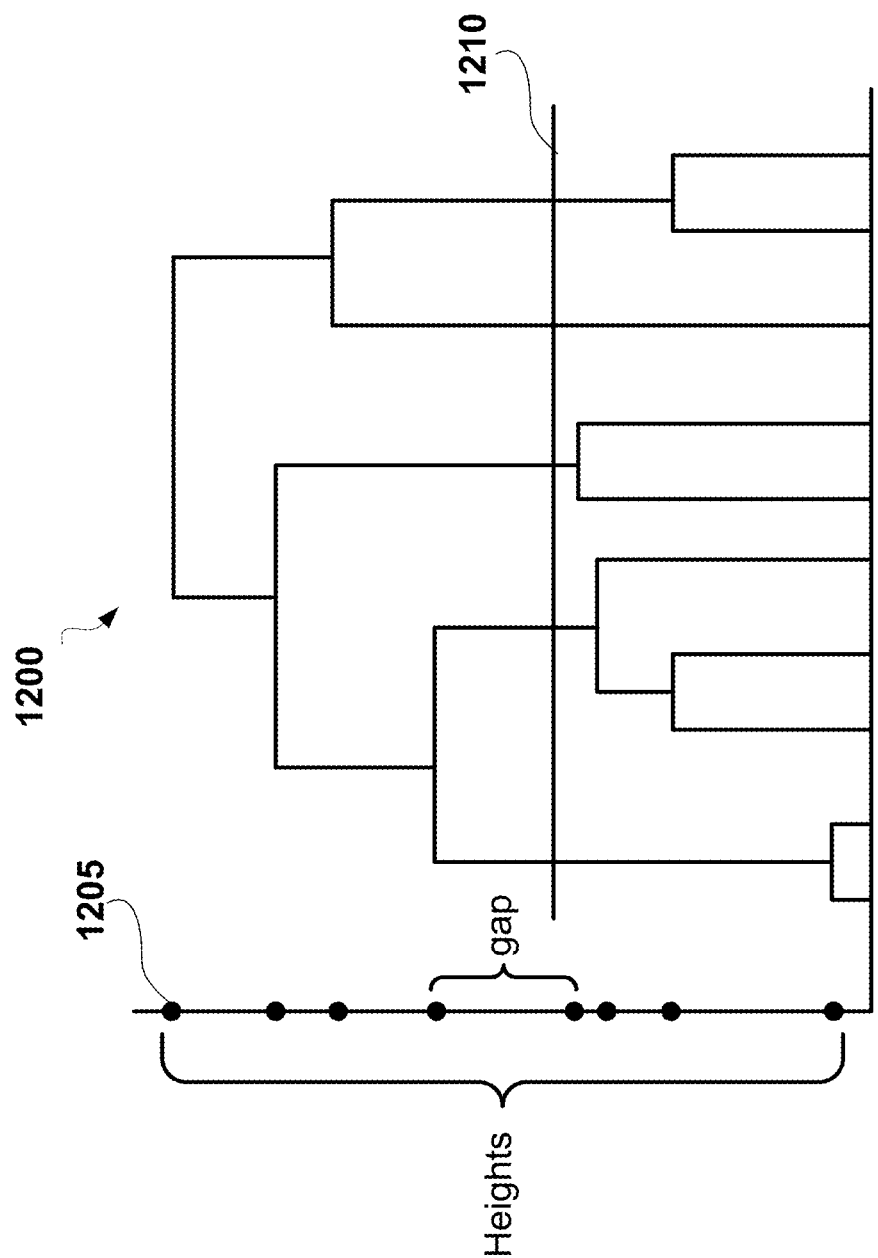
FIG. 12 depicts a tree of clusters, according to an example embodiment.

FIG. 12 depicts a tree 1200 of clusters, according to an example embodiment. The tree 1200 of clusters is also referred to as a dendrogram 1200. The dendrogram is a presentation of hierarchical clustering of projection values belonging to the same domain of overlapping domains. The projection values are obtained by projections of the data points $\{x(k)=(x_1(k), x_2(k), \ldots, x_n(k))\}$. In some embodiments with one dimensional projections, the heights 1205 are length of intervals [a, b] within the domain. Each level in the dendrogram 1200 shows how many of the clusters can be obtained by clustering all projection values belonging to the interval [a, b]. At the largest value of the height 1205, the interval [a, b] corresponds to the entire domain, therefore, all projection values can be collected into a single cluster. Thus, the dendrogram 1200 includes only one cluster at the largest value of the height 1205. When the height 1205 decreases, the number of clusters (also referred to as connectivity components) in the dendrogram 1200 increases. Thus, the height 1205 may represent a level of granularity for clustering the projection values within the same domain from the set of overlapping domains. The clustering can be carried out using various methods, such as, for example, single-linkage clustering, complete clustering, average clustering, and weighted clustering.

As shown in the FIG. 12, there is a set of discrete values of the height 1205 at which the number of the clusters in the dendrogram 1200 changes and there are gaps between the discrete values with the number of clusters remaining the same. In some embodiments of the present disclosure, an optimal level of granularity, that is an optimal height 1210, can be determined for each domain of the overlapping domains. The nodes in the metric graph can be connected if their corresponding projection values belong to a cluster obtained with the optimal level of granularity.

The optimal level of granularity can be selected within any gap between the heights 1205. In example of FIG. 12, the optimal level of granularity (the optimal height 1210) corresponds to a level at which the dendrogram 1200 includes four connectivity components (clusters).

Figure 13:
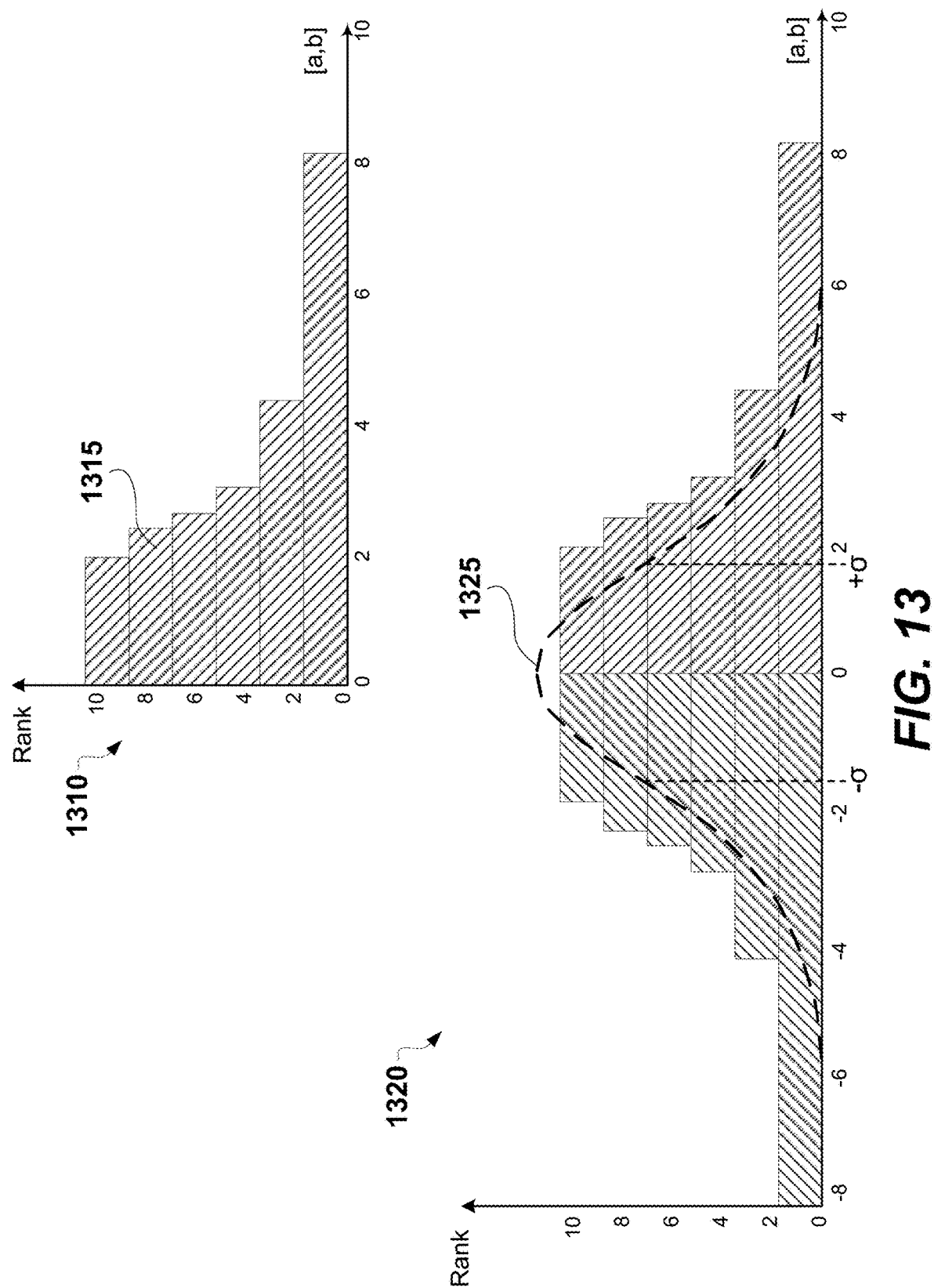
FIG. 13 depicts a histogram used for determining the optimal level of granularity, according to some example embodiments.

FIG. 13 depicts a histogram 1310 that can be used for determining the optimal level of granularity, according to some embodiments. In the histogram 1310, each level 1315 represents a tuple. The first element of the tuple is the number of clusters. The second element of the tuple is an interval [a, b] (the height 1205) corresponding to this number of clusters in the dendrogram 1200. The histogram 1310 is rotated by 90 degrees clockwise. The rotated histogram 1310 can be flipped to obtain the histogram 1320. The histogram 1320 can be approximated by a Gaussian distribution 1325. A standard deviation σ of the distribution 1325 can be found and used to determine the optimal height 1205.

The optimal height 1210 can be selected to be above or at the standard deviation σ. This selection ensures that the metric graph within a domain from the set of overlapping does not fall apart into many small connected components. The optimal height 1205 may satisfy an additional condition: the number of connected components (clusters) does not exceed a certain threshold. The threshold can be equal to half the set of projection values belonging to the domain for which the optimal height 1205 is determined.

Referring back to FIG. 12, the optimal height 1210 is located within a gap between two discrete values of the height 1205. In some embodiments, in order to obtain the metric graph with minimum number of edges, the lower bound of the gap can be selected as the optimal height 1210.

After the optimal heights (the optimal levels of granularity) are selected for each domain of the overlapping domains, the metric graph can be built by connecting a pair of nodes in the set of nodes, if this pair of nodes can be connected by an edge in at least one subgraph of the domain. In this sense, a metric graph can be understood as a union of intermediate metric graphs for separate domains with the removal of duplicate edges.

Thus, the systems and methods for graph-based discovery of geometry of clinical data have been described. Although embodiments have been described with reference to specific example embodiments, it will be evident that various modifications and changes can be made to these example embodiments without departing from the broader spirit and scope of the present document. Accordingly, the specification and drawings are to be regarded in an illustrative rather than a restrictive sense.

What is claimed is:

1. A system for graph-based discovery of geometry of clinical data, the system comprising:
   at least one processor; and
   a memory communicatively coupled with the at least one processor, the memory storing instructions, which when executed by the at least processor performs a method comprising:
      receiving vectors of outcomes of trial subjects;
      generating, based on the vectors of outcomes, a plurality of metric graphs, each of the metric graphs including:
         a same set of nodes corresponding to the vectors of outcomes; and
         a set of edges, wherein generating the set of edges includes:
            transforming the vectors of outcomes to generate data points;
            selecting a projection rule from a set of projection rules;
            applying the selected projection rule to the data points to obtain projections of the vectors of outcomes; and
            for each of a first node and a second node from the same set of nodes:
               determining that a first projection and a second projection of the projections satisfy similarity criteria, the first projection corresponding to the first node and the second projection corresponding to the second node; and based on the determination, selectively connecting the first node and the second node;

selecting, from the plurality of metric graphs, an optimal graph;

performing an automatic search to identify at least one community of nodes in the optimal graph;

displaying a graphical representation of the optimal graph; and highlighting nodes in the graphical representation, the nodes corresponding to the at least one community of nodes.

2. The system of claim 1, wherein:

the transformation of the vectors of outcomes includes:

selecting a first metric from a set of metrics; and applying the first metric to the vectors of outcomes to generate data points; and the projection rule depends on a second metric of the set of metrics.

3. The system of claim 2, wherein the set of metrics includes:

one or more of the following or a weighted combination of: a Euclidean distance, a normalized Euclidean distance, a Manhattan distance, a Hamming distance, a Gower distance, and a Minkowski distance; and a complex metric obtained as a weighted sum of metrics determined on subsets of components of the vectors of outcomes.

4. The system of claim 1, wherein the determining that the first projection and the second projection satisfy the similarity criteria includes determining that the first projection and the second projection are located within a same domain in a set of overlapping domains.

5. The system of claim 4, wherein each of the set of overlapping domains has the same size.

6. The system of claim 4, wherein each of the set of overlapping domains contains a same number of the projections.

7. The system of claim 4, wherein the determining that the first projection and the second projection satisfy the similarity criteria further includes:

constructing a tree of clusters of the projections belonging to the same domain and by varying a level of granularity; and determining that the first projection and the second projection belong to a same cluster from the tree of clusters, wherein the same cluster obtained with an optimal level of granularity obtained for the same domain.

8. The system of claim 7, wherein a number of clusters corresponding to the optimal level of granularity is less than a half of a total number of the projections in the same domain.

9. The system of claim 7, wherein a number of clusters corresponding to the optimal value of granularity exceeds a minimum of a standard deviation of numbers of clusters obtained using a set of values for the level of granularity.

10. The system of claim 7, wherein the optimal level of granularity for the projections belonging to the same domain differs from a further optimal level of granularity obtained for a further domain of the set of overlapping domains.

11. A method for graph-based discovery of geometry of clinical data, the method comprising:

receiving vectors of outcomes of trial subjects;

generating, based on the vectors of outcomes, a plurality of metric graphs, each of the metric graphs including:

a same set of nodes corresponding to the vectors of outcomes; and a set of edges, wherein generating the set of edges includes:

transforming the vectors of outcomes to generate data points;

selecting a projection rule from a set of projection rules;

applying the selected projection rule to the data points to obtain projections of the vectors of outcomes; and for each of a first node and a second node from the same set of nodes:

determining that a first projection and a second projection of the projections satisfy similarity criteria, the first projection corresponding to the first node and the second projection corresponding to the second node; and based on the determination, selectively connecting the first node and the second node;

selecting, from the plurality of metric graphs, an optimal graph;

performing an automatic search to identify at least one community of nodes in the optimal graph;

displaying a graphical representation of the optimal graph; and highlighting nodes in the graphical representation, the nodes corresponding to the at least one community of nodes.

12. The method of claim 11, wherein:

the transformation of the vectors of outcomes includes:

selecting a first metric from a set of metrics; and applying the first metric to the vectors of outcomes to generate data points; and the projection rule depends on a second metric of the set of metrics.

13. The method of claim 11, wherein the set of metrics includes:

one or more of the following or a weighted combination of: a Euclidean distance, a normalized Euclidean distance, a Manhattan distance, a Hamming distance, a Gower distance, and a Minkowski distance; and a complex metric obtained as a weighted sum of metrics determined on subsets of components of the vectors of outcomes.

14. The method of claim 11, wherein the determining that the first projection and the second projection satisfy the similarity criteria includes determining that the first projection and the second projection are located within a same domain in a set of overlapping domains.

15. The method of claim 14, wherein each of the set of overlapping domains has the same size.

16. The method of claim 14, wherein each of the set of overlapping domains contains a same number of the projections.

17. The method of claim 14, wherein the determining that the first projection and the second projection satisfy the similarity criteria further includes:

constructing a tree of clusters of the projections belonging to the same domain and by varying a level of granularity; and determining that the first projection and the second projection belong to a same cluster from the tree of clusters, wherein the same cluster obtained with an optimal level of granularity obtained for the same domain.

18. The method of claim 17, wherein a number of clusters corresponding to the optimal level of granularity is less than a half of a total number of the projections in the same domain.

19. The method of claim 17, wherein a number of clusters corresponding to the optimal value of granularity exceeds a minimum of a standard deviation of numbers of clusters obtained using a set of values for the level of granularity.

20. A non-transitory computer-readable storage medium having embodied thereon instructions, which when executed by at least one processor, perform steps of a method, the method comprising:
　　receiving vectors of outcomes of trial subjects;
　　generating, based on the vectors of outcomes, a plurality of metric graphs, each of the metric graphs including:
　　　　a same set of nodes corresponding to the vectors of outcomes; and
　　　　a set of edges, wherein generating the set of edges includes:
　　　　　　transforming the vectors of outcomes to generate data points;
　　　　　　selecting a projection rule from a set of projection rules;
　　　　　　applying the selected projection rule to the data points to obtain projections of the vectors of outcomes; and
　　　　　　for each of a first node and a second node from the same set of nodes:
　　　　　　　　determining that a first projection and a second projection of the projections satisfy similarity criteria, the first projection corresponding to the first node and the second projection corresponding to the second node; and
　　　　　　　　based on the determination, selectively connecting the first node and the second node;
　　selecting, from the plurality of metric graphs, an optimal graph;
　　performing an automatic search to identify at least one community of nodes in the optimal graph;
　　displaying a graphical representation of the optimal graph; and
　　highlighting nodes in the graphical representation, the nodes corresponding to the at least one community of nodes.

* * * * *